(12) United States Patent
Watanabe et al.

(10) Patent No.: US 12,033,318 B2
(45) Date of Patent: Jul. 9, 2024

(54) ESTIMATION APPARATUS, ESTIMATION SYSTEM, AND COMPUTER-READABLE NON-TRANSITORY MEDIUM STORING ESTIMATION PROGRAM

(71) Applicants: KYOCERA Corporation, Kyoto (JP); The University of Tokyo, Tokyo (JP)

(72) Inventors: Kenichi Watanabe, Tokyo (JP); Masayuki Kyomoto, Ritto (JP); Shintaro Honda, Tokyo (JP); Toru Moro, Tokyo (JP); Sakae Tanaka, Tokyo (JP)

(73) Assignees: Kyocera Corporation, Kyoto (JP); The University of Tokyo, Tokyo (JP)

( * ) Notice: Subject to any disclaimer, the term of this patent is extended or adjusted under 35 U.S.C. 154(b) by 338 days.

(21) Appl. No.: 17/274,757

(22) PCT Filed: Sep. 10, 2019

(86) PCT No.: PCT/JP2019/035594
§ 371 (c)(1),
(2) Date: Mar. 9, 2021

(87) PCT Pub. No.: WO2020/054738
PCT Pub. Date: Mar. 19, 2020

(65) Prior Publication Data
US 2022/0051398 A1    Feb. 17, 2022

(30) Foreign Application Priority Data

Sep. 10, 2018  (JP) .................................. 2018-168502
Nov. 26, 2018  (JP) .................................. 2018-220401

(51) Int. Cl.
G06T 7/00   (2017.01)
A61B 6/50   (2024.01)
G06T 7/11   (2017.01)

(52) U.S. Cl.
CPC ............ *G06T 7/0012* (2013.01); *A61B 6/505* (2013.01); *G06T 7/11* (2017.01);
(Continued)

(58) Field of Classification Search
None
See application file for complete search history.

(56) References Cited

U.S. PATENT DOCUMENTS 5,259,384 A    11/1993 Kaufman et al.
5,931,780 A    8/1999 Giger et al.
(Continued)

FOREIGN PATENT DOCUMENTS

CA    2158033 A1    8/1996
CN    107485405 A    12/2017
(Continued)

OTHER PUBLICATIONS

González, Germán, George R. Washko, and Raúl San José Estépar. "Deep learning for biomarker regression: application to osteoporosis and emphysema on chest CT scans." Medical Imaging 2018: Image Processing. vol. 10574. SPIE, 2018. (Year: 2018).*

(Continued)

*Primary Examiner* — Samah A Beg
(74) *Attorney, Agent, or Firm* — Procopio, Cory, Hargreaves Savitch LLP

(57) ABSTRACT

An estimation apparatus includes an input unit and an approximator. Input information including an image in which a bone appears is input into the input unit. The approximator is configured to determine an estimation result related to bone density of the bone from the input information. The approximator includes a learned parameter to obtain the estimation result.

33 Claims, 14 Drawing Sheets

(52) U.S. Cl.
CPC ............... *G06T 2207/10116* (2013.01); *G06T 2207/20081* (2013.01); *G06T 2207/20084* (2013.01); *G06T 2207/30008* (2013.01); *G06T 2207/30096* (2013.01)

(56) References Cited

U.S. PATENT DOCUMENTS

| | | | |
|---|---|---|---|
| 6,064,716 A * | 5/2000 | Siffert | ............... A61B 6/482 378/53 |
| 6,246,745 B1 | 6/2001 | Bi et al. | |
| 6,430,427 B1 | 8/2002 | Lee et al. | |
| 6,570,955 B1 | 5/2003 | Siffert et al. | |
| 2001/0002925 A1 | 6/2001 | Siffert et al. | |
| 2002/0025063 A1 | 2/2002 | Jiang et al. | |
| 2002/0156378 A1 | 10/2002 | Sakai | |
| 2006/0120583 A1 | 6/2006 | Dewaele | |
| 2009/0285467 A1 | 11/2009 | Chen et al. | |
| 2009/0297012 A1 | 12/2009 | Brett et al. | |
| 2010/0310141 A1 | 12/2010 | Wilson | |
| 2016/0015347 A1* | 1/2016 | Bregman-Amitai | ........................ G06T 7/0012 382/131 |
| 2018/0025255 A1 | 1/2018 | Poole et al. | |
| 2018/0140282 A1 | 5/2018 | Toyomura et al. | |
| 2019/0150176 A1 | 5/2019 | Pelletier et al. | |
| 2020/0069243 A1 | 3/2020 | Matsumoto et al. | |

FOREIGN PATENT DOCUMENTS

| | | |
|---|---|---|
| EP | 1357480 A1 | 10/2003 |
| JP | H9-248292 A | 9/1997 |
| JP | H09-508813 A | 9/1997 |
| JP | H11-192223 A | 7/1999 |
| JP | 2000-245722 A | 9/2000 |
| JP | 2002-523204 A | 7/2002 |
| JP | 2002-238904 A | 8/2002 |
| JP | 2004-00556 A | 1/2004 |
| JP | 2006-136724 A | 6/2006 |
| JP | 2007-52774 A | 3/2007 |
| JP | 2007-524438 A | 8/2007 |
| JP | 2008-036068 A | 2/2008 |
| JP | 2009-515594 A | 4/2009 |
| JP | 2011-523573 A | 8/2011 |
| JP | 2012-139411 A | 7/2012 |
| JP | 2014-158628 A | 9/2014 |
| JP | 2016-106720 A | 6/2016 |
| JP | 2018-011958 A | 1/2018 |
| JP | 2019-515594 A | 6/2019 |
| JP | 2022-156223 A | 10/2022 |
| KR | 10-2018-0029476 A | 3/2018 |
| WO | 1995/14431 A1 | 6/1995 |
| WO | 2004/086972 A2 | 10/2004 |
| WO | 2016/194161 A1 | 12/2016 |
| WO | 2017/141958 A1 | 8/2017 |

OTHER PUBLICATIONS

Kawathekar, Pooja P., and Kailash J. Karande. "Severity analysis of Osteoarthritis of knee joint from X-ray images: A Literature review." 2014 International Conference on Signal propagation and computer technology (ICSPCT 2014). IEEE, 2014. (Year: 2014).*

Khan, Shiyana Sherief, Archana S. Jayan, and Sharmila Nageswaran. "An image processing algorithm to estimate bone mineral density using digital X-ray images." 2017 Second International Conference on Electrical, Computer and Communication Technologies (ICECCT). IEEE, 2017. (Year: 2017).*

Whitmarsh, Tristan, et al. "3D reconstruction of the lumbar vertebrae from anteroposterior and lateral dual-energy X-ray absorptiometry." Medical image analysis 17.4 (2013): 475-487. (Year: 2013).*

Gonzalez et al., "Deep Learning for Biomarker Regression. Application to Osteoporosis and Emphysema on Chest CT Scans", Proc. of SPIE vol. 10574 105741H-1, 6 pages.

Chu et al., "Using Octuplet Siamese Network for Osteoporosis Analysis on Dental Panoramic Radiographs". 978-1-5386-3646-6/18, 2018 IEEE, p. 2579-2582.

Kroger et al., "Diagnosis of osteoporosis in clinical practice", Trends in Clinical Practice, The Finnish Medical Society Duodecim, Ann Wed 1998; 30: p. 278-287.

Decision to Grant a Patent for the corresponding JP Application No. JP2022-075792 dated Aug. 30, 2022, 6 pages.

Written Opinion for the corresponding JP Application No. JP2022-075792 dated Aug. 9, 2022, 4 pages.

Notice of Reasons for Refusal for the corresponding JP Application No. JP2022-075792 dated Jun. 14, 2022, 12 pages.

International Search Report and Written Opinion of the International Searching Authority for the corresponding PCT Application No. PCT/JP2019/035594 dated Nov. 5, 2019, 19 pages.

* cited by examiner

F I G. 1 4
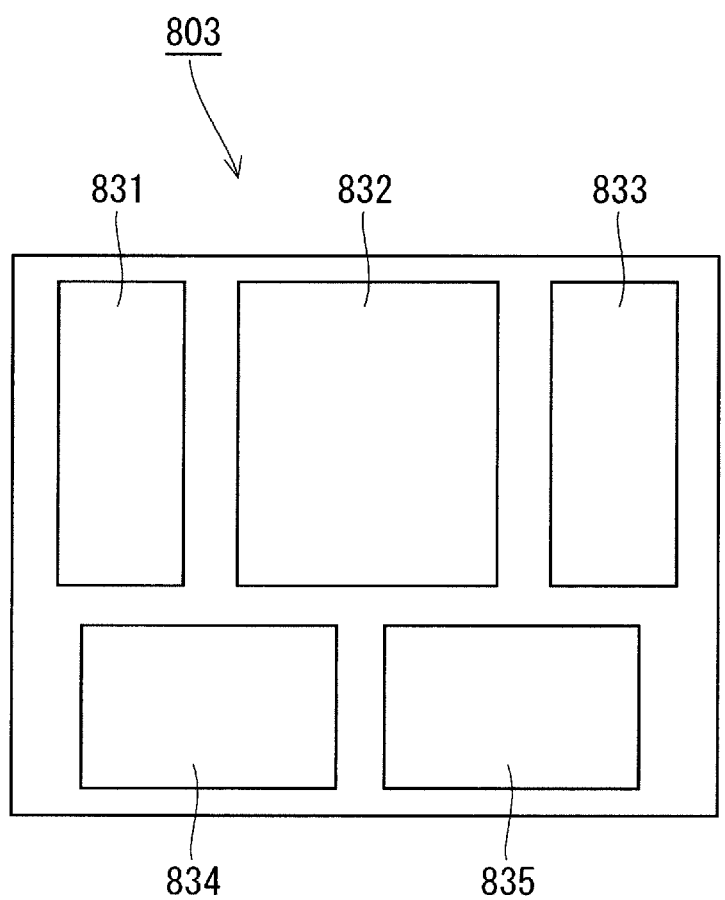

F I G. 1 5
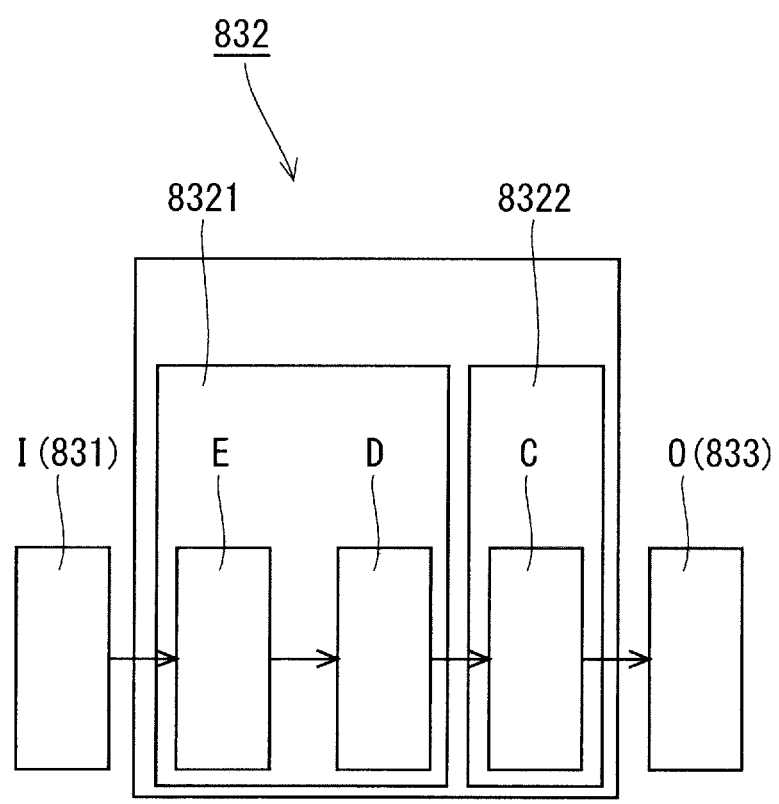

F I G. 1 7
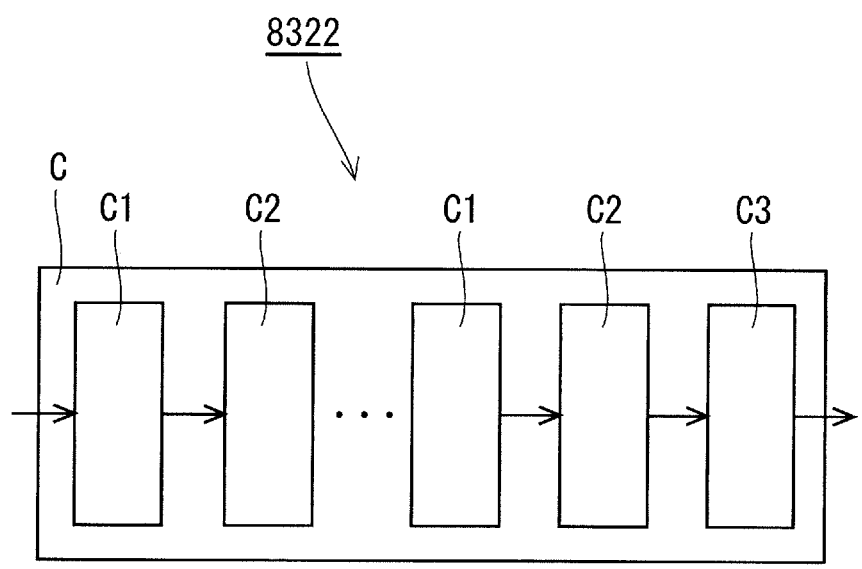
F I G. 1 8
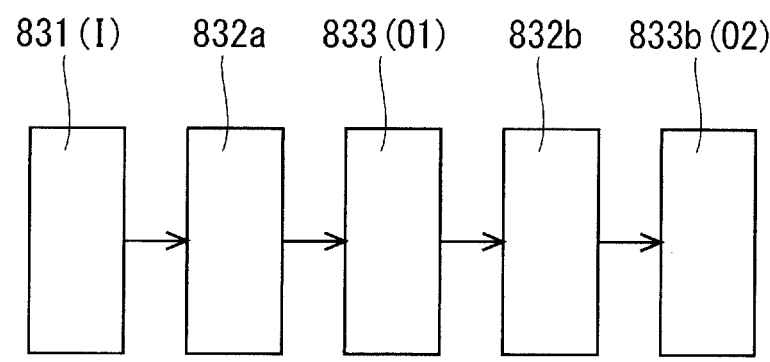

ESTIMATION APPARATUS, ESTIMATION SYSTEM, AND COMPUTER-READABLE NON-TRANSITORY MEDIUM STORING ESTIMATION PROGRAM

CROSS-REFERENCE TO RELATED APPLICATION

The present application is a National Phase entry based on PCT Application No. PCT/JP2019/035594 filed on Sep. 10, 2019, entitled "ESTIMATION DEVICE, ESTIMATION SYSTEM, AND ESTIMATION PROGRAM", which claims the benefit of Japanese Patent Application No. 2018-168502, filed on Sep. 10, 2018, entitled "BONE DENSITY ESTIMATION PROGRAM, BONE DENSITY ESTIMATION DEVICE, AND BONE DENSITY ESTIMATION SYSTEM" and Japanese Patent Application No. 2018-220401, filed on Nov. 26, 2018, entitled "ESTIMATION SYSTEM". The content of which is incorporated by reference herein in its entirety.

FIELD

Embodiments of the present disclosure relates to estimation of bone density.

BACKGROUND

Patent Document 1 discloses technology for determining osteoporosis. Patent Document 2 discloses technology for estimating bone strength.

SUMMARY

An estimation apparatus, an estimation system, and an estimation program are disclosed. In one embodiment, the estimation apparatus is an estimation apparatus including an input unit, an approximator, and an output unit. Input information including an image in which a bone appears is input into the input unit. The approximator is configured to determine an estimation result related to bone density of the bone from the input information. The output unit outputs the estimation result determined by the approximator. The approximator includes a learned parameter to obtain the estimation result.

In one embodiment, the estimation system includes an input unit and an approximator. Input information including an image in which a bone appears is input into the input unit. The approximator includes a learned parameter to obtain an estimation result related to bone density of the bone from the input information, and is configured to determine the estimation result related to the bone density of the bone from the input information input into the input unit. The approximator performs operations on the input information when the input information is input into the input unit.

In one embodiment, the estimation program is an estimation program to cause an apparatus to function as a neural network. The neural network is configured to perform operations based on a learned parameter to obtain an estimation result related to bone density of a bone from input information including an image in which the bone appears, and output an estimated value of the bone density of the bone appearing in the image.

BRIEF DESCRIPTION OF THE DRAWINGS

FIG. 14 illustrates a conceptual diagram schematically showing a configuration of a portion of the estimation system.

FIG. 15 illustrates a conceptual diagram schematically showing a configuration of a portion of the estimation system.

FIG. 17 illustrates a conceptual diagram schematically showing a configuration of a portion of the estimation system.

FIG. 18 illustrates a conceptual diagram schematically showing a configuration of a portion in another embodiment of the disclosure of the estimation system.

DETAILED DESCRIPTION

Embodiment 1

Figure 1:
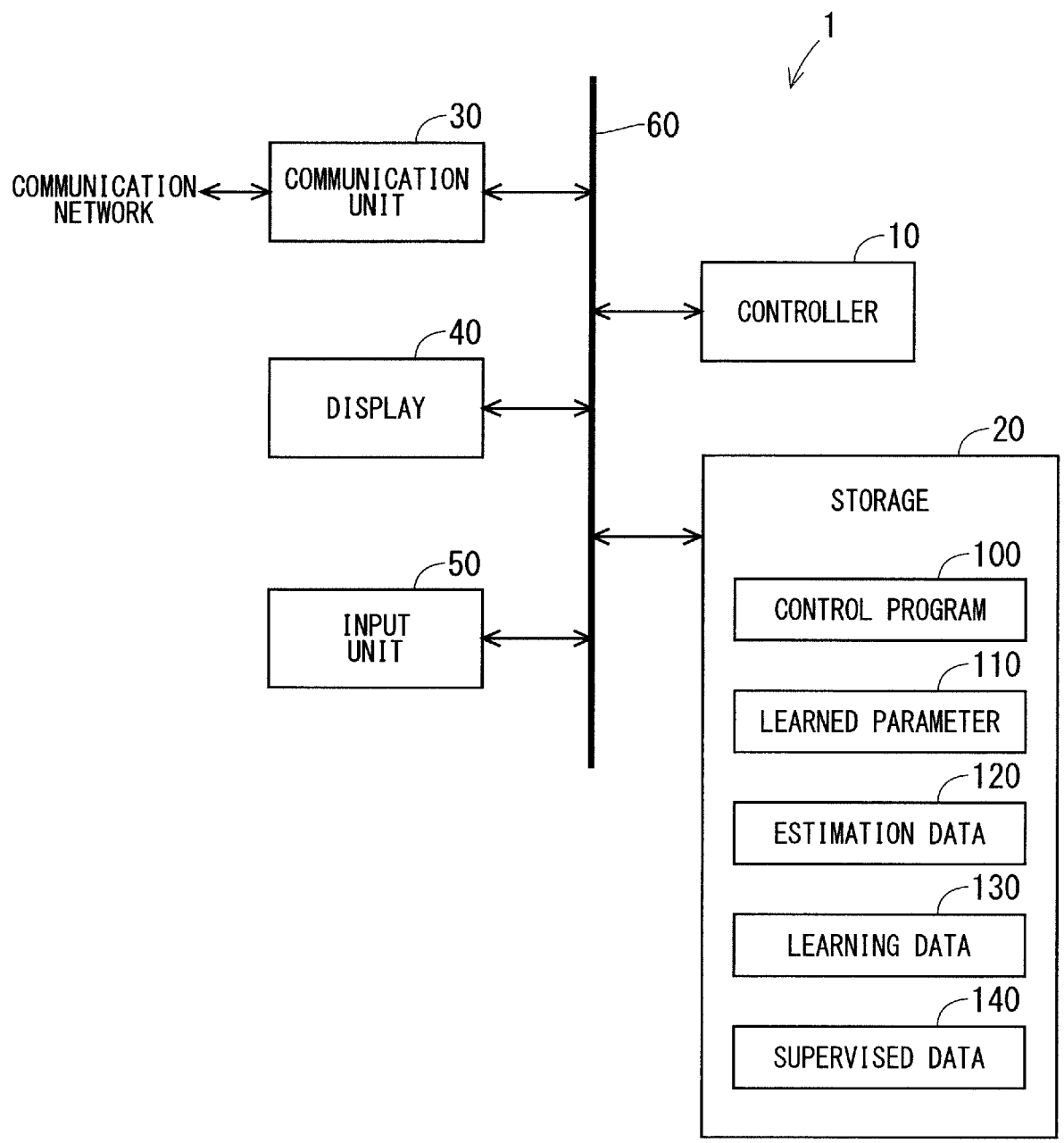
FIG. 1 illustrates a diagram showing one example of a configuration of a computer apparatus (an estimation apparatus).

FIG. 1 illustrates a block diagram showing one example of a configuration of a computer apparatus 1 in Embodiment 1. The computer apparatus 1 functions as an estimation apparatus to estimate bone density. The computer apparatus 1 is hereinafter also referred to as an "estimation apparatus 1".

As shown in FIG. 1, the estimation apparatus 1 includes a controller 10, a storage 20, a communication unit 30, a display 40, and an input unit 50, for example. The controller 10, the storage 20, the communication unit 30, the display 40, and the input unit 50 are electrically connected to one another via a bus 60, for example.

The controller 10 can provide overall management of operation of the estimation apparatus 1 through control of the other components of the estimation apparatus 1. It can be said that the controller 10 is a control device or a control circuit. The controller 10 includes at least one processor for providing control and processing capability to perform various functions as described in further detail below.

In accordance with various embodiments, the at least one processor may be implemented as a single integrated circuit (IC) or as multiple communicatively coupled ICs and/or discrete circuits. It is appreciated that the at least one processor can be implemented in accordance with various known technologies.

In one embodiment, the processor includes one or more circuits or units configurable to perform one or more data computing procedures or processes by executing instructions stored in associated memory, for example. In other embodiments, the processor may be implemented as firmware (e.g., discrete logic components) configured to perform one or more data computing procedures or processes.

In accordance with various embodiments, the processor may include one or more processors, controllers, microprocessors, microcontrollers, application specific integrated circuits (ASICs), digital signal processors, programmable logic devices, field programmable gate arrays, or any combination of these devices or structures, or other known devices and structures, to perform the functions described herein. In this example, the controller 10 includes a central processing unit (CPU), for example.

Figure 2:
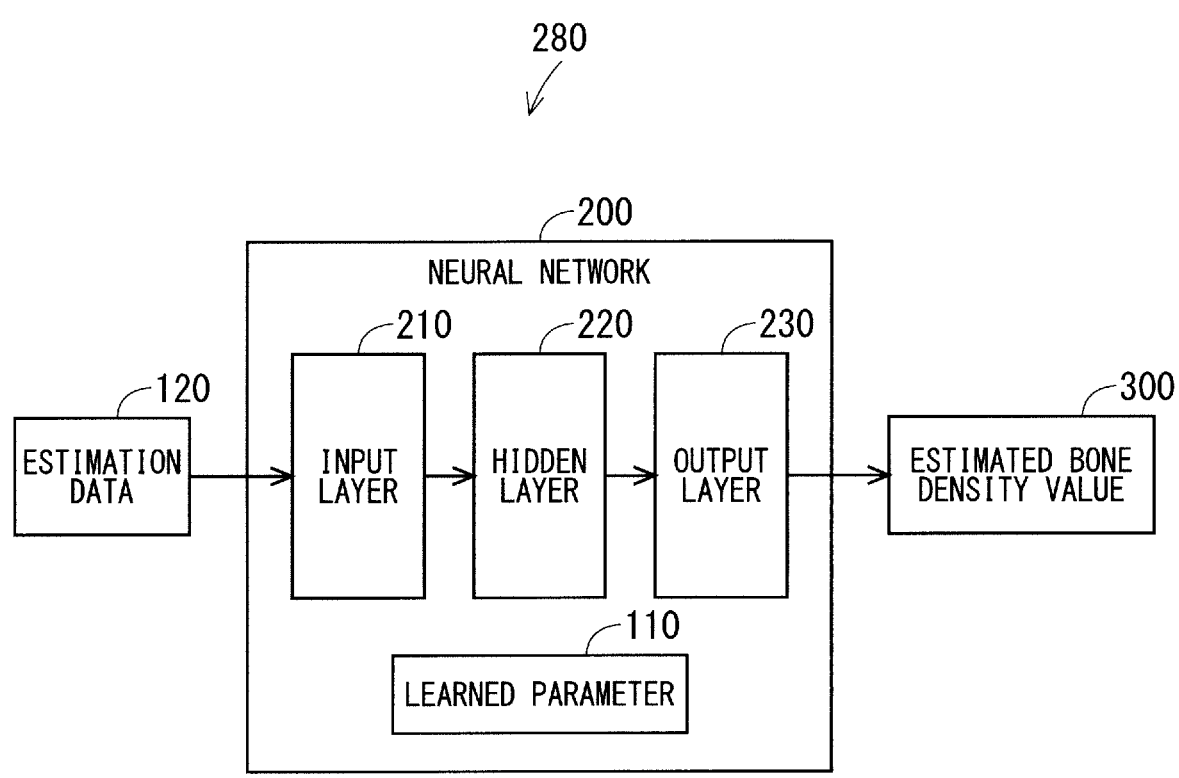
FIG. 2 illustrates a diagram for explaining operation of the estimation apparatus.

The storage 20 includes a non-transitory recording medium readable by the CPU of the controller 10, such as read only memory (ROM) and random access memory (RAM). A control program 100 to control the estimation apparatus 1 is stored in the storage 20. Various functions of the controller 10 are performed by the CPU of the controller 10 executing the control program 100 in the storage 20. It can be said that the control program 100 is a bone density estimation program to cause the computer apparatus 1 to function as the estimation apparatus. In this example, by the controller 10 executing the control program 100 in the storage 20, an approximator 280 that can output an estimated value 300 of bone density is formed in the controller 10 as shown in FIG. 2. The approximator 280 includes a neural network 200, for example. It can be said that the control program 100 is a program to cause the computer apparatus 1 to function as the neural network 200. The estimated value of bone density is hereinafter also referred to as an "estimated bone density value". An example of a configuration of the neural network 200 will be described in detail below.

In addition to the control program 100, a learned parameter 110, estimation data 120 (hereinafter, also referred to as "input information"), learning data 130, and supervised data 140 related to the neural network 200 are stored in the storage 20. The learning data 130 and the supervised data 140 are data used when the neural network 200 is learned. The learned parameter 110 and the estimation data 120 are data used in a case where the learned neural network 200 estimates bone density.

The learning data 130 is data input into an input layer 210 of the neural network 200 when the neural network 200 is learned. The learning data 130 is also referred to as learn data. The supervised data 140 is data indicating a correct value of bone density. The supervised data 140 is compared with output data output from an output layer 230 of the neural network 200 when the neural network 200 is learned. The learning data 130 and the supervised data 140 are also collectively referred to as supervised learn data.

The estimation data 120 is data input, in a case where the learned neural network 200 estimates bone density, into the input layer 210 thereof. The learned parameter 110 is a learned parameter in the neural network 200. It can be said that the learned parameter 110 is a parameter adjusted through learning of the neural network 200. The learned parameter 110 includes a weighting factor indicating the weight of a connection between artificial neurons. The learned neural network 200 performs operations on the estimation data 120 input into the input layer 210 based on the learned parameter 110, and outputs the estimated bone density value 300 from the output layer 230 as shown in FIG. 2.

Data may be input into the input layer 210 through the input unit 50, or may directly be input into the input layer 210. In a case where data is directly input into the input layer 210, the input layer 210 may be part or all of the input unit 50. The estimated bone density value 300 is hereinafter also referred to as an estimation result 300.

The communication unit 30 is connected to a communication network including the Internet and the like through a wire or wirelessly. The communication unit 30 can communicate with another device, such as a cloud server and a web server, via the communication network. The communication unit 30 can input information received via the communication network into the controller 10. The communication unit 30 can also output information received from the controller 10 via the communication network.

The display 40 is a liquid crystal display or an organic EL display, for example. The display 40 can display various pieces of information, such as characters, symbols, and graphics, by being controlled by the controller 10.

The input unit 50 can receive input from a user into the estimation apparatus 1. The input unit 50 includes a keyboard and a mouse, for example. The input unit 50 may include a touch panel that can detect operation of the user on a display surface of the display 40.

The configuration of the estimation apparatus 1 is not limited to that in the above-mentioned example. For example, the controller 10 may include a plurality of CPUs. The controller 10 may include at least one DSP. All or part of the function of the controller 10 may be performed by a hardware circuit not requiring software to perform the function. The storage 20 may include a computer-readable non-transitory recording medium other than the ROM and the RAM. The storage 20 may include a miniature hard disk drive and a solid state drive (SSD), for example. The storage 20 may include memory, such as universal serial bus (USB) memory, removable from the estimation apparatus 1. The memory removable from the estimation apparatus 1 is hereinafter also referred to as "removable memory".

Example of Configuration of Neural Network

Figure 3:
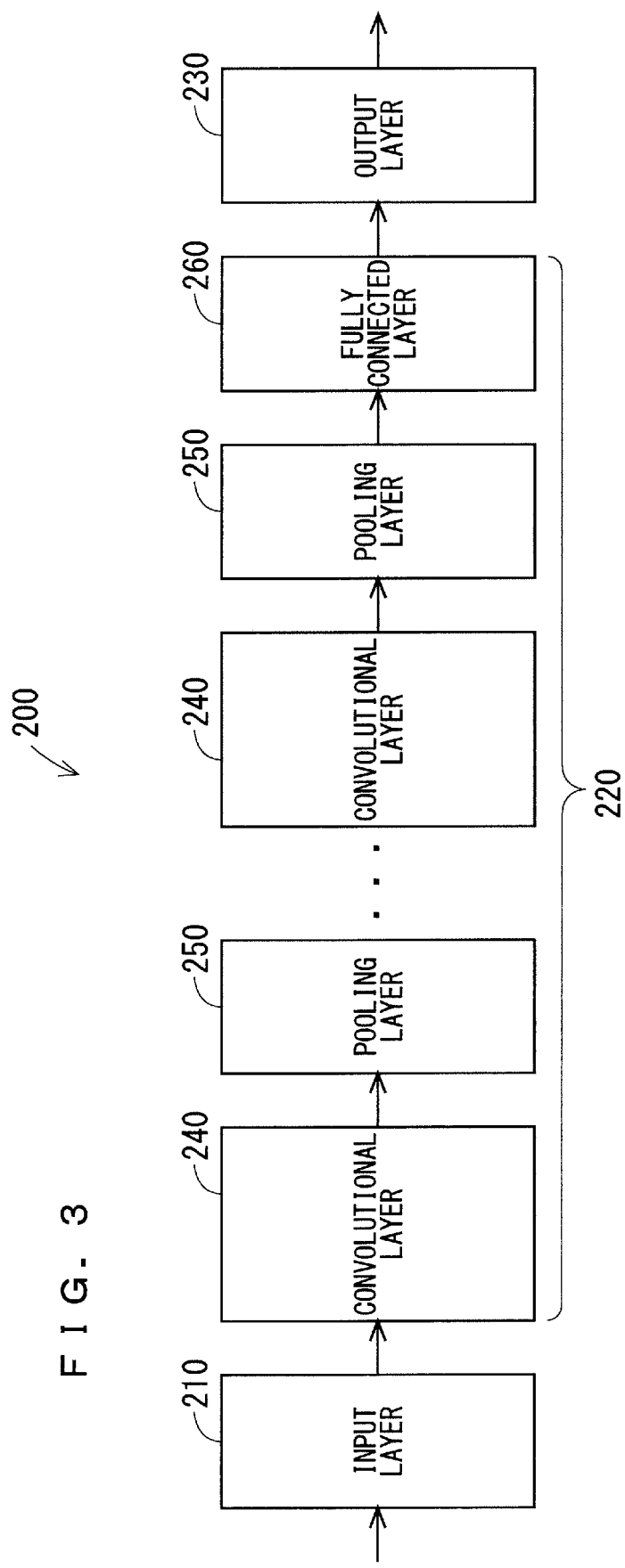
FIG. 3 illustrates a diagram showing one example of a configuration of a neural network.

FIG. 3 illustrates a diagram showing one example of the configuration of the neural network 200. In this example, the neural network 200 is a convolutional neural network (CNN), for example. As shown in FIG. 3, the neural network 200 includes the input layer 210, a hidden layer 220, and the output layer 230, for example. The hidden layer 220 is also referred to as an intermediate layer. The hidden layer 220 includes a plurality of convolutional layers 240, a plurality of pooling layers 250, and a fully connected layer 260, for example. In the neural network 200, the fully connected layer 260 precedes the output layer 230. In the neural network 200, the convolutional layers 240 and the pooling layers 250 are alternately arranged between the input layer 210 and the fully connected layer 260.

The configuration of the neural network 200 is not limited to that in the example of FIG. 3. For example, the neural network 200 may include a single convolutional layer 240 and a single pooling layer 250 between the input layer 210 and the fully connected layer 260. The neural network 200 may be a neural network other than the CNN.

Examples of Estimation Data, Learning Data, and Supervised Data

The estimation data 120 includes image data of a plain X-ray image in which a bone of a target of estimation of bone density appears. The target of estimation of bone density is a person, for example. It can thus be said that the estimation data 120 includes image data of a plain X-ray image in which a bone of a person appears. The learning data 130 includes image data pieces of a plurality of plain X-ray images in each of which a bone of a person appears. A plain X-ray image is a two-dimensional image, and is also referred to as a general X-ray image or a radiographic image. The target of estimation of bone density may not be a person. The target of estimation of bone density may be an animal, such as a dog, a cat, and a horse. A bone of interest mainly includes a cortical bone and a cancellous bone derived from organisms, but may include an artificial bone containing calcium phosphate as a main component and a regenerated bone artificially manufactured by regenerative medicine and the like.

The image data included in the estimation data 120 is hereinafter also referred to as "estimation image data". The plain X-ray image indicated by the image data included in the estimation data 120 is hereinafter also referred to as an "estimation plain X-ray image". The image data pieces included in the learning data 130 are hereinafter also referred to as "learning image data pieces". The plain X-ray images indicated by the image data pieces included in the learning data 130 are hereinafter also referred to as "learning plain X-ray images". The learning data 130 includes a plurality of learning X-ray image data pieces indicating the respective learning plain X-ray images.

For example, a head, a neck, a chest, a waist, a hip joint, a knee joint, an ankle joint, a foot, a toe, a shoulder joint, an elbow joint, a wrist joint, a hand, a finger, or a temporomandibular joint is used as an imaging part of the estimation plain X-ray image. In other words, used as the estimation data 120 is image data of a plain X-ray image obtained by X-ray exposure to the head, image data of a plain X-ray image obtained by X-ray exposure to the neck, image data of a plain X-ray image obtained by X-ray exposure to the chest, image data of a plain X-ray image obtained by X-ray exposure to the waist, image data of a plain X-ray image obtained by X-ray exposure to the hip joint, image data of a plain X-ray image obtained by X-ray exposure to the knee joint, image data of a plain X-ray image obtained by X-ray exposure to the ankle joint, image data of a plain X-ray image obtained by X-ray exposure to the foot, image data of a plain X-ray image obtained by X-ray exposure to the toe, image data of a plain X-ray image obtained by X-ray exposure to the shoulder joint, image data of a plain X-ray image obtained by X-ray exposure to the elbow joint, image data of a plain X-ray image obtained by X-ray exposure to the wrist joint, image data of a plain X-ray image obtained by X-ray exposure to the hand, image data of a plain X-ray image obtained by X-ray exposure to the finger, or image data of a plain X-ray image obtained by X-ray exposure to the temporomandibular joint. The plain X-ray image obtained by X-ray exposure to the chest includes a plain X-ray image in which a lung appears and a plain X-ray image in which a thoracic vertebra appears. The type of the imaging part of the estimation plain X-ray image is not limited to these examples. The estimation plain X-ray image may be a frontal image in which the front of the part of interest appears or a side image in which the side of the part of interest appears.

An imaging part of each of the learning plain X-ray images indicated by the respective learning image data pieces included in the learning data 130 includes at least one of the head, the neck, the chest, the waist, the hip joint, the knee joint, the ankle joint, the foot, the toe, the shoulder joint, the elbow joint, the wrist joint, the hand, the finger, and/or the temporomandibular joint, for example. In other words, the learning data 130 includes at least one of 15 types of image data including the image data of the plain X-ray image obtained by X-ray exposure to the head, the image data of the plain X-ray image obtained by X-ray exposure to the neck, the image data of the plain X-ray image obtained by X-ray exposure to the chest, the image data of the plain X-ray image obtained by X-ray exposure to the waist, the image data of the plain X-ray image obtained by X-ray exposure to the hip joint, the image data of the plain X-ray image obtained by X-ray exposure to the knee joint, the image data of the plain X-ray image obtained by X-ray exposure to the ankle joint, the image data of the plain X-ray image obtained by X-ray exposure to the foot, the image data of the plain X-ray image obtained by X-ray exposure to the toe, the image data of the plain X-ray image obtained by X-ray exposure to the shoulder joint, the image data of the plain X-ray image obtained by X-ray exposure to the elbow joint, the image data of the plain X-ray image obtained by X-ray exposure to the wrist joint, the image data of the plain X-ray image obtained by X-ray exposure to the hand, the image data of the plain X-ray image obtained by X-ray exposure to the finger, and/or the image data of the plain X-ray image obtained by X-ray exposure to the temporomandibular joint. The learning data 130 may include some or all of the 15 types of image data. The imaging part of each of the learning plain X-ray images is not limited to these examples. The learning plain X-ray images may include the frontal image and the side image. The learning plain X-ray images may include both the frontal image and the side image of the same imaging part.

The supervised data 140 includes, for each of the learning image data pieces included in the learning data 130, a measured value of bone density of a person having a bone appearing in a learning plain X-ray image indicated by the learning image data. Measured values of bone density included in the supervised data 140 include at least one of a measured value of bone density measured by X-ray exposure to a lumbar vertebra, bone density measured by X-ray exposure to a proximal femur, bone density measured by X-ray exposure to a radius, bone density measured by X-ray exposure to a metacarpal, bone density measured by ultrasonic exposure to an arm, and/or bone density measured by ultrasonic exposure to a heel, for example. A measured value of bone density included in the supervised data 140 is hereinafter also referred to as "reference bone density".

Dual-energy X-ray absorptiometry (DEXA) is herein known as a method for measuring bone density. In a DEXA apparatus to measure bone density by DEXA, the front of the lumbar vertebra is exposed to X-rays (specifically, two types of X-rays) in a case where bone density of the lumbar vertebra is measured. In the DEXA apparatus, the front of the proximal femur is exposed to X-rays in a case where bone density of the proximal femur is measured.

The supervised data 140 may include bone density of the lumbar vertebra measured by the DEXA apparatus and bone density of the proximal femur measured by the DEXA apparatus. The supervised data 140 may include bone density measured by X-ray exposure to the side of the part of interest. The supervised data 140 may include bone density measured by X-ray exposure to the side of the lumbar vertebra, for example.

An ultrasonic method is known as another method for measuring bone density. In an apparatus to measure bone density by the ultrasonic method, the arm is exposed to ultrasonic waves to measure bone density of the arm, and the heel is exposed to ultrasonic waves to measure bone density of the heel. The supervised data 140 may include bone density measured by the ultrasonic method.

Figure 4:
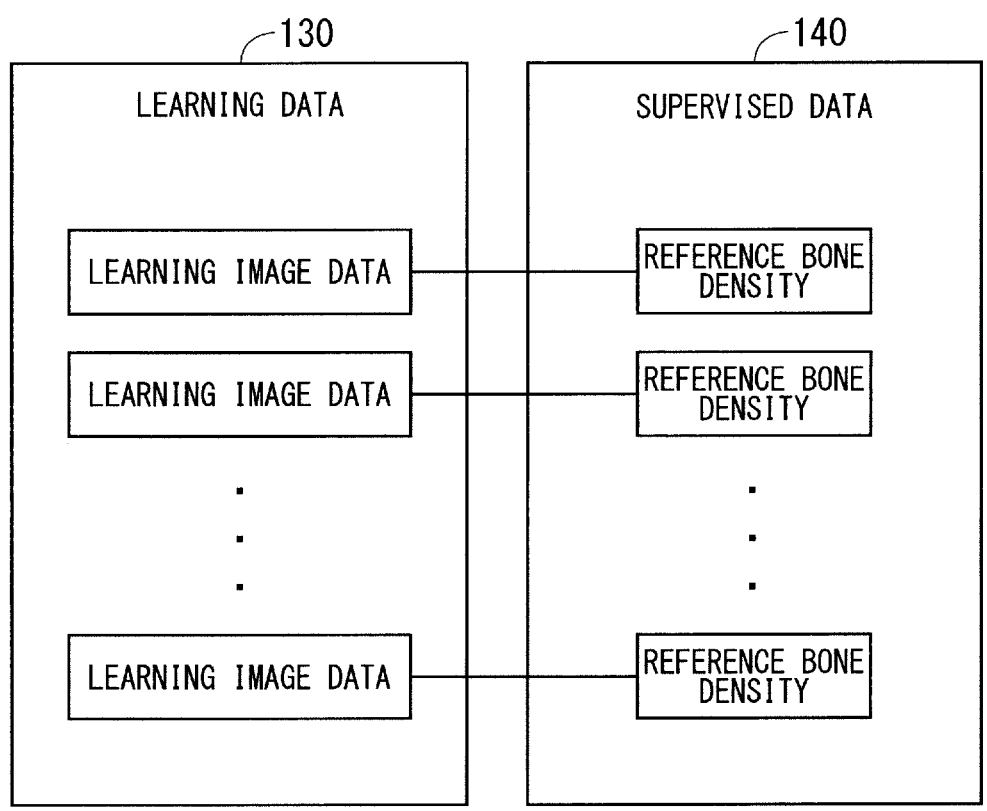
FIG. 4 illustrates a diagram showing one example of a state of learning image data and reference bone density being associated with each other.

Bones of a plurality of different people appear in the learning plain X-ray images indicated by the respective learning image data pieces included in the learning data 130. As shown in FIG. 4, with each of the learning image data pieces included in the learning data 130, reference bone density of a person having a bone appearing in a learning plain X-ray image indicated by the learning image data is associated in the storage 20. It can be said that, with each of the learning plain X-ray images used in learning of the neural network 200, reference bone density of a person having a bone appearing in the learning plain X-ray image is associated. Reference bone density associated with the learning image data is bone density of the same person as the person having a bone appearing in the learning plain X-ray image indicated by the learning image data measured in approximately the same time period as a time period in which the learning plain X-ray image is taken.

A part appearing in the learning plain X-ray image indicated by the learning image data (i.e., the imaging part of the learning plain X-ray image) may include a part (i.e., bone) from which reference bone density associated with the learning image data is measured or may not include the part from which reference bone density associated with the learning image data is measured. In other words, the part appearing in the learning plain X-ray image may include the part from which reference bone density associated with the learning plain X-ray image is measured or may not include the part from which reference bone density associated with the learning plain X-ray image is measured. A case where learning image data indicating a learning plain X-ray image in which the waist appears and reference bone density of the lumbar vertebra are associated with each other is considered as an example of the former. A case where learning image data in which the hip joint appears and reference bone density of the proximal femur are associated with each other is considered as another example of the former. On the other hand, a case where learning image data in which the chest appears and reference bone density of the lumbar vertebra are associated with each other is considered as an example of the latter. A case where learning image data in which the knee joint appears and reference bone density of the heel are associated with each other is considered as another example of the latter.

A direction of the part appearing in the plain X-ray image indicated by the learning image data and a direction of X-ray exposure to the part of interest in measurement of reference bone density associated with the learning image data may be the same or may be different. In other words, the direction of the part appearing in the learning plain X-ray image and the direction of X-ray exposure to the part of interest in measurement of reference bone density associated with the learning plain X-ray image may be the same or may be different. A case where learning image data indicating a plain X-ray image in which the front of the chest appears (hereinafter, also referred to as a "chest front plain X-ray image") and reference bone density measured by X-ray exposure to the front of the lumbar vertebra are associated with each other is considered as an example of the former. A case where learning image data indicating a plain X-ray image in which the front of the waist appears (hereinafter, also referred to as a "waist front plain X-ray image") and reference bone density measured by X-ray exposure to the front of the proximal femur are associated with each other is considered as another example of the former. On the other hand, a case where learning image data indicating a plain X-ray image in which the side of the waist appears (hereinafter, also referred to as a "waist side plain X-ray image") and reference bone density measured by X-ray exposure to the front of the lumbar vertebra are associated with each other is considered as an example of the latter. A case where learning image data indicating a plain X-ray image in which the side of the knee joint appears (hereinafter, also referred to as a "knee side plain X-ray image") and reference bone density measured by X-ray exposure to the front of the proximal femur are associated with each other is considered as another example of the latter.

The learning plain X-ray images indicated by the respective learning image data pieces included in the learning data 130 may include a plain X-ray image in which a part of the same type as a part appearing in the estimation plain X-ray image appears, or may include a plain X-ray image in which a part of a different type from the part appearing in the estimation plain X-ray image appears. A case where the learning plain X-ray images include the chest front plain X-ray image when the estimation plain X-ray image is the chest front plain X-ray image is considered as an example of the former. A case where the learning plain X-ray images include the knee side plain X-ray image when the estimation plain X-ray image is a plain X-ray image in which the front of the knee joint appears (hereinafter, also referred to as a "knee front plain X-ray image") is considered as another example of the former. On the other hand, a case where the learning plain X-ray images include the chest front plain X-ray image when the estimation plain X-ray image is the waist front plain X-ray image is considered as an example of the latter. A case where the learning plain X-ray images include the knee front plain X-ray image when the estimation plain X-ray image is the waist side plain X-ray image is considered as another example of the latter.

The learning plain X-ray images may include a plain X-ray image in which a part in the same direction as the part appearing in the estimation plain X-ray image appears, or may include a plain X-ray image in which a part in a different direction from the part appearing in the estimation plain X-ray image appears. A case where the learning plain X-ray images include the waist front plain X-ray image when the estimation plain X-ray image is a lumbar vertebra front plain X-ray image is considered as an example of the former. A case where the learning plain X-ray images include the chest front plain X-ray image when the estimation plain X-ray image is the knee front plain X-ray image is considered as another example of the former. On the other hand, a case where the learning plain X-ray images include the knee front plain X-ray image when the estimation plain X-ray image is the knee side plain X-ray image is considered as an example of the latter. A case where the learning plain X-ray images include the chest front plain X-ray image when the estimation plain X-ray image is the waist side plain X-ray image is considered as another example of the latter.

The supervised data 140 may include reference bone density measured from a part (bone) included in the part appearing in the estimation plain X-ray image or may include reference bone density measured from a part (bone) not included in the part appearing in the estimation plain X-ray image. A case where the supervised data 140 includes reference bone density of the lumbar vertebra when the estimation plain X-ray image is the waist front plain X-ray image is considered as an example of the former. On the other hand, a case where the supervised data 140 includes reference bone density of the metacarpal when the estimation plain X-ray image is the chest front plain X-ray image is considered as an example of the latter.

The supervised data 140 may include reference bone density measured by X-ray exposure to the part of interest from the same direction as the part appearing in the estimation plain X-ray image or may include reference bone density measured by X-ray exposure to the part of interest from a different direction from the part appearing in the estimation plain X-ray image. A case where the supervised data 140 includes reference bone density measured by X-ray exposure to the lumbar vertebra from the front thereof when the estimation plain X-ray image is the waist front plain X-ray image is considered as an example of the former. On the other hand, a case where the supervised data 140 includes reference bone density measured by X-ray exposure to the proximal femur from the front thereof when the estimation plain X-ray image is the waist side plain X-ray image is considered as an example of the latter.

In this example, data obtained by reducing grayscale image data indicating a plain X-ray image taken by a plain X-ray imaging apparatus (i.e., a general X-ray imaging apparatus or a radiographic imaging apparatus) and reducing the number of gray levels thereof is used as the learning image data and the estimation image data. Consider a case where the number of a plurality of pixels data pieces constituting the image data obtained by the plain X-ray imaging apparatus is greater than 1024×640, and the number of bits of the pixel data pieces is 16, for example. In this case, data obtained by reducing the number of pixels data pieces constituting the image data obtained by the plain X-ray imaging apparatus to 256×256, 1024×512, or 1024×640, and reducing the number of bits of the pixel data pieces to 8, for example, is used as the learning image data and the estimation image data. In this case, each of the learning plain X-ray image and the estimation plain X-ray image is composed of 256×256 pixels, 1024×512 pixels, or 1024×640 pixels, and values of the pixels are expressed in 8 bits.

The learning image data and the estimation image data may be generated by the controller 10 of the estimation apparatus 1 from image data obtained by the plain X-ray imaging apparatus or may be generated by an apparatus other than the estimation apparatus 1 from image data obtained by the plain X-ray imaging apparatus. In the former case, the image data obtained by the plain X-ray imaging apparatus may be received by the communication unit 30 via the communication network, or may be stored in the removable memory included in the storage 20. In the latter case, the communication unit 30 may receive the learning image data and the estimation image data from the other apparatus via the communication network, and the controller 10 may store the learning image data and the estimation image data received by the communication unit 30 in the storage 20. Alternatively, the learning image data and the estimation image data generated by the other apparatus may be stored in the removable memory included in the storage 20. The supervised data 140 may be received by the communication unit 30 via the communication network, and the controller 10 may store the supervised data 140 received by the communication unit 30 in the storage 20. Alternatively, the supervised data 140 may be stored in the removable memory included in the storage 20. The number of pixel data pieces and the number of bits of the pixel data pieces of each of the learning image data and the estimation image data are not limited to the above-mentioned examples.

Example of Learning of Neural Network

Figure 5:
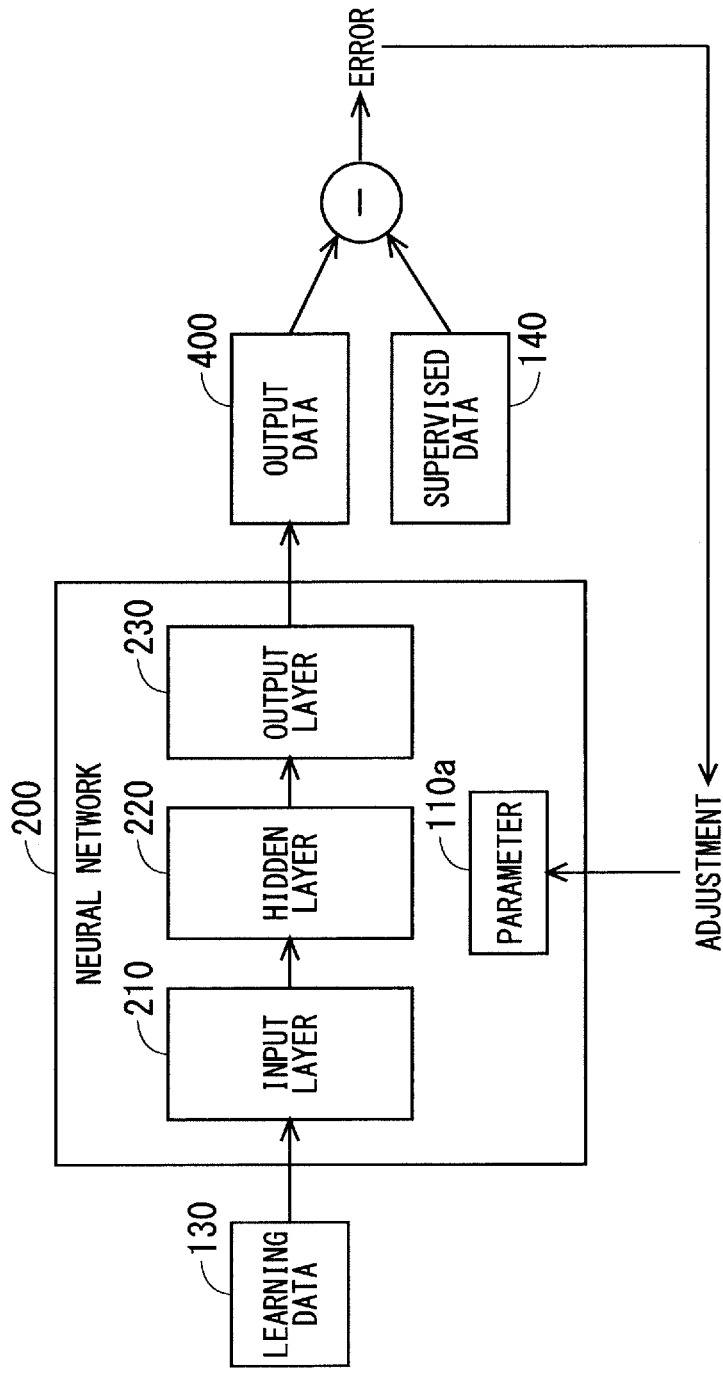
FIG. 5 illustrates a diagram for explaining operation of the estimation apparatus.

FIG. 5 illustrates a diagram for explaining one example of learning of the neural network 200. When the neural network 200 is learned, the controller 10 inputs the learning data 130 into the input layer 210 of the neural network 200 as shown in FIG. 5. The controller 10 adjusts a variable parameter 110a in the neural network 200 to reduce an error, from the supervised data 140, of the output data 400 output from the output layer 230 of the neural network 200. More specifically, the controller 10 inputs each of the learning image data pieces in the storage 20 into the input layer 210. When inputting the learning image data into the input layer 210, the controller 10 inputs a plurality of pixel data pieces constituting the learning image data into respective artificial neurons constituting the input layer 210. The controller 10 adjusts the parameter 110a to reduce an error, from reference bone density associated with the learning image data, of the output data 400 output from the output layer 230 when the learning image data is input into the input layer 210. Backpropagation is used as a method for adjusting the parameter 110a, for example. The parameter 110a as adjusted is stored in the storage 20 as the learned parameter 110. The parameter 110a includes a parameter used in the hidden layer 220, for example. Specifically, the parameter 110a includes a filter factor used in the convolutional layer 240 and the weighting factor used in the fully connected layer 260. The method for adjusting the parameter 110a, that is, a method for learning the parameter 110a, is not limited to this method.

As described above, the learning data 130 including the image data pieces of the respective learning plain X-ray images and the learned parameter 110 obtained by learning the relationship with the measured value of bone density as the supervised data 140 using the neural network 200 are stored in the storage 20.

The estimation apparatus 1 performs learning of the neural network 200 in the above-mentioned example, but another apparatus may perform learning of the neural network 200. In this case, the learned parameter 110 generated by the other apparatus is stored in the storage 20 of the estimation apparatus 1. Storing the learning data 130 and the supervised data 140 in the storage 20 becomes unnecessary. The learned parameter 110 generated by the other apparatus may be received by the communication unit 30 via the communication network, and the controller 10 may store the learned parameter 110 received by the communication unit 30 in the storage 20. Alternatively, the learned parameter 110 generated by the other apparatus may be stored in the removable memory included in the storage 20.

The neural network 200 learned as described above includes the learned parameter 110a learned by the image data pieces of the respective learning plain X-ray images being input into the input layer 210 as the learning data 130, and using reference bone density as the supervised data 140. As shown in FIG. 2 described above, the neural network 200 performs operations on the estimation data 120 input into the input layer 210 based on the learned parameter 110a, and outputs the estimated bone density value 300 from the output layer 230. When the estimation image data as the estimation data 120 is input into the input layer 210, a plurality of pixel data pieces constituting the estimation image data are input into the respective artificial neurons constituting the input layer 210. The convolutional layer 240 performs operations using the filter factor included in the learned parameter 110a, and the fully connected layer 260 performs operations using the weighting factor included in the learned parameter 110a.

For example, when the estimation image data indicating the chest front plain X-ray image is input into the input layer 210, the estimated value 300 of bone density of a person having a bone of the chest appearing in the chest front plain X-ray image indicated by the estimation image data is output from the output layer 230. When the estimation image data indicating the waist front plain X-ray image is input into the input layer 210, the estimated value 300 of bone density of a person having the lumbar vertebra included in the waist appearing in the waist front plain X-ray image indicated by the estimation image data is output from the output layer 230. When the estimation image data indicating the waist side plain X-ray image is input into the input layer 210, the estimated value 300 of bone density of a person having the lumbar vertebra included in the waist appearing in the waist side plain X-ray image indicated by the estimation image data is output from the output layer 230. When the estimation image data indicating the knee front plain X-ray image is input into the input layer 210, the estimated value 300 of bone density of a person having a bone of the knee joint appearing in the knee front plain X-ray image indicated by the estimation image data is output from the output layer 230. When the estimation image data indicating the knee side plain X-ray image is input into the input layer 210, the estimated value 300 of bone density of a person having a bone of the knee joint appearing in the knee side plain X-ray image indicated by the estimation image data is output from the output layer 230.

The estimated value 300 output from the output layer 230 may be represented by at least one of bone mineral density per unit area ($g/cm^2$), bone mineral density per unit volume ($g/cm^3$), YAM, a T-score, and/or a Z-score. YAM stands for "young adult mean", and is also referred to as a young adult average percent. For example, the estimated value 300 represented by the bone mineral density per unit area ($g/cm^2$) and the estimated value 300 represented by the YAM may be output from the output layer 230, or the estimated value 300 represented by the YAM, the estimated value 300 represented by the T-score, and the estimated value 300 represented by the Z-score may be output from the output layer 230.

The storage 20 may store a plurality of estimation data pieces 120. In this case, a plurality of estimation plain X-ray images indicated by the respective estimation data pieces 120 in the storage 20 may include a plurality of plain X-ray images in which parts of the same type appear, or may include a plurality of plain X-ray images in which parts of different types appear. The plurality of estimation plain X-ray images may include a plurality of plain X-ray images in which parts from the same direction appear, or may include a plurality of plain X-ray images in which parts from different directions appear. In other words, the plurality of estimation plain X-ray images may include a plurality of plain X-ray images in which parts in the same direction appear, or may include a plurality of plain X-ray images in which parts in different directions appear. The controller 10 inputs each of the plurality of estimation data pieces 120 in the storage 20 into the input layer 210 of the neural network 200, and estimated bone density values 300 corresponding to the respective estimation data pieces 120 are output from the output layer 230 of the neural network 200.

As described above, in this example, learning of the neural network 200 and estimation of bone density by the neural network 200 are performed using the image data pieces of the plain X-ray images. The image data pieces of the plain X-ray images, that is, image data pieces of radiographic images are used in various examinations and the like in many hospitals, and are thus easily available. Bone density can thus easily be estimated without using an expensive apparatus, such as the DEXA apparatus.

By using image data of a plain X-ray image taken for an examination and the like as the estimation image data, bone density can easily be estimated using the opportunity for the examination and the like. Use of the estimation apparatus 1 can thus improve services for hospital users.

A bone may be less likely to appear in a front plain X-ray image, such as the chest front plain X-ray image, due to the influence of organs. On the other hand, the front plain X-ray image is likely to be taken in many hospitals. In this example, bone density can be estimated even if the front plain X-ray image in which a bone may be less likely to appear is used as the estimation plain X-ray image or the learning plain X-ray image. Bone density can thus easily be estimated using image data of the front plain X-ray image that is easily available. It can be said that the chest front plain X-ray image is a plain X-ray image that is particularly easily available as it is often taken in physical examinations and the like. By using the chest front plain X-ray image as the estimation plain X-ray image or the learning plain X-ray image, bone density can more easily be estimated.

In this example, bone density can be estimated from the image data of the estimation plain X-ray image even if the plurality of learning plain X-ray images include the plain X-ray image in which the part of the different type from the part appearing in the estimation plain X-ray image appears. Usability of the estimation apparatus 1 (i.e., computer apparatus 1) can thereby be improved.

In this example, bone density can be estimated from the image data of the estimation plain X-ray image even if the plurality of learning plain X-ray images include the plain X-ray image in which the part in the different direction from the part appearing in the estimation plain X-ray image appears. Usability of the estimation apparatus 1 can thereby be improved.

In this example, the neural network 200 can estimate bone density based on the learned parameter 110 even if the part appearing in the learning plain X-ray image does not include the part (bone) from which reference bone density associated with the learning plain X-ray image is measured. Usability of the estimation apparatus 1 can thereby be improved.

In this example, the neural network 200 can estimate bone density based on the learned parameter 110 even if the direction of the part appearing in the learning plain X-ray image and the direction of X-ray exposure to the part of interest in measurement of reference bone density associated with the learning plain X-ray image are different from each other. Usability of the estimation apparatus 1 can thereby be improved.

In this example, bone density can be estimated from the image data of the estimation plain X-ray image even if the supervised data 140 includes reference bone density measured from the part not included in the part appearing in the estimation plain X-ray image. Usability of the estimation apparatus 1 can thereby be improved.

The estimated bone density value 300 obtained by the estimation apparatus 1 may be displayed by the display 40. The estimated bone density value 300 obtained by the estimation apparatus 1 may be used by another apparatus.

Figure 6:
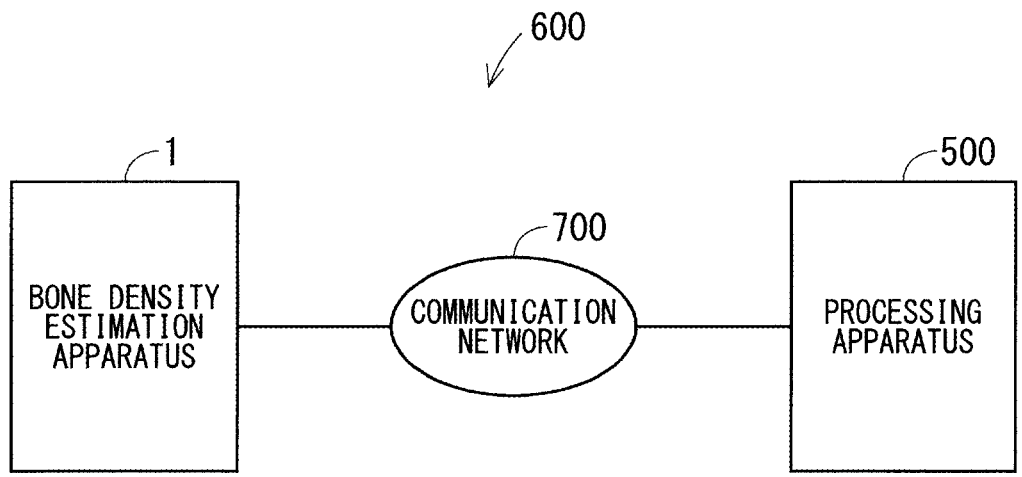
FIG. 6 illustrates a diagram showing one example of an estimation system.

FIG. 6 illustrates a diagram showing one example of a bone density estimation system 600 including the estimation apparatus 1 and a processing apparatus 500 to perform processing using the estimated bone density value 300 obtained by the estimation apparatus 1. In the example of FIG. 6, the estimation apparatus 1 and the processing apparatus 500 can communicate with each other via a communication network 700. The communication network 700 includes at least one of a wireless network and/or a wired network, for example. The communication network 700 includes a wireless local area network (LAN) and the Internet, for example.

The communication network 700 is connected to the communication unit 30 in the estimation apparatus 1. The controller 10 causes the communication unit 30 to transmit the estimated bone density value 300 to the processing apparatus 500. The processing apparatus 500 performs processing using the estimated bone density value 300 received from the estimation apparatus 1 via the communication network 700. For example, the processing apparatus 500 is a display, such as a liquid crystal display, and displays the estimated bone density value 300. In this case, the processing apparatus 500 may display the estimated bone density value 300 as a table or as a graph. In a case where a plurality of estimation apparatuses 1 are connected to the communication network 700, the processing apparatus 500 may display estimated bone density values 300 obtained by the plurality of estimation apparatuses 1. The processing apparatus 500 may have the same configuration as the estimation apparatus 1 shown in FIG. 1, or may have a different configuration from the estimation apparatus 1 shown in FIG. 1.

Processing using the estimated bone density value 300 performed by the processing apparatus 500 is not limited to the above-mentioned example. The processing apparatus 500 may directly communicate with the estimation apparatus 1 wirelessly or through a wire not via the communication network 700.

Other Examples of Estimation Data and Learning Data

First Other Examples

In this example, the learning data 130 includes, for each of the learning image data pieces, information related to a health condition of a person having a bone appearing in a learning plain X-ray image indicated by the learning image data. In other words, the learning data 130 includes, for each of the learning image data pieces, information related to a health condition of a subject (test subject) of the learning plain X-ray image indicated by the learning image data. The information related to the health condition of the subject of the learning plain X-ray image is hereinafter also referred to as "learning health-related information". The information related to the health condition of the subject of the learning plain X-ray image indicated by the learning image data is also referred to as the learning health-related information corresponding to the learning image data.

The learning health-related information includes at least one of age information, gender information, height information, weight information, drinking habit information, smoking habit information, and/or fracture history information, for example. A database of the learning health-related information is compiled for each person, and the learning health-related information is generated as a comma-separated value (CSV) format file or a text format file. Each of the age information, the height information, and the weight information is expressed as a plurality of bits of numerical data, for example. The gender information is expressed as one bit of data indicating "male" or "female", and the drinking habit information is expressed as one bit of data indicating "with drinking habit" or "without drinking habit", for example. The smoking habit information is expressed as one bit of data indicating "with smoking habit" or "without smoking habit", and the fracture history information is expressed as one bit of data indicating "with fracture history" or "without fracture history". The learning health-related information may include a body fat percentage or a percentage of fat under the skin of the test subject.

In a case where the learning data 130 includes the learning image data and the learning health-related information corresponding to the learning image data, reference bone density (see FIG. 4) associated with the learning image data is also associated with the learning health-related information corresponding to the learning image data. That is to say, with learning image data indicating a learning plain X-ray image in which a bone of a certain person appears and information related to a health condition (the learning health-related information) of the person, a measured value of bone density (reference bone density) of the person is associated. In learning of the neural network 200, the learning image data and the learning health-related information corresponding to the learning image data are simultaneously input into the input layer 210. Specifically, the learning image data is input into a part of the plurality of artificial neurons constituting the input layer 210, and the learning health-related information is input into the other part of the artificial neurons. The output data 400 output from the output layer 230 when the learning image data and the learning health-related information corresponding to the learning image data are input into the input layer 210 and reference bone density associated with the learning image data and the learning health-related information are compared with each other.

In this example, the estimation data 120 includes the estimation image data and information related to a health condition of a person having a bone appearing in the estimation plain X-ray image indicated by the estimation image data. In other words, the estimation data 120 includes the estimation image data and information related to a health condition of the subject of the estimation plain X-ray image indicated by the estimation image data. The information related to the health condition of the subject of the estimation plain X-ray image is hereinafter also referred to as "estimation health-related information (hereinafter also referred to as "individual data" in the other embodiments)". The information related to the health condition of the subject of the estimation plain X-ray image indicated by the estimation image data is also referred to as the estimation health-related information corresponding to the estimation image data.

As with the learning health-related information, the estimation health-related information includes at least one of the age information, the gender information, the height information, the weight information, the drinking habit information, the smoking habit information, and/or the fracture history information, for example. The estimation health-related information includes information of the same type as the learning health-related information. As with the learning health-related information, the estimation health-related information may include the body fat percentage or the percentage of fat under the skin of the test subject.

In this example, in a case where bone density is estimated, the estimation image data and the estimation health-related information corresponding to the estimation image data are simultaneously input into the input layer 210. Specifically, the estimation image data is input into a part of the plurality of artificial neurons constituting the input layer 210, and the estimation health-related information is input into the other part of the artificial neurons. When the estimation image data and the estimation health-related information of a certain person are input into the input layer 210, an estimated value of bone density of the person is output from the output layer 230.

As described above, the accuracy of estimation of bone density can be improved by using not only the image data of the plain X-ray image but also information related to the health condition of the subject of the plain X-ray image.

Second Other Examples

In this example, the learning data 130 includes image data pieces of N (N≥2) learning plain X-ray images in which parts of the same person appear and the parts are in different directions. The N learning plain X-ray images are hereinafter also collectively referred to as a "learning plain X-ray image set".

The learning plain X-ray image set includes a frontal image and a side image of the same person, for example. The learning plain X-ray image set includes the chest front plain X-ray image and the waist side plain X-ray image of a certain person, for example. Image sizes of the frontal image and the side image included in the learning plain X-ray image set may be different from each other. For example, the image size of the side image may have a smaller width than the image size of the frontal image. Image data pieces of the respective learning plain X-ray images of the learning plain X-ray image set are hereinafter also collectively referred to as a "learning image data set".

The learning data 130 includes learning image data sets of a plurality of different people. The learning data 130 thus includes a plurality of learning image data sets. One reference bone density is associated with each of the learning image data sets. That is to say, with a learning image data set of a certain person, a measured value of bone density (reference bone density) of the person is associated.

In learning of the neural network 200 in this example, each of the learning image data sets is input into the input layer 210. In a case where a single learning image data set is input into the input layer 210, N learning image data pieces constituting the single learning image data set are simultaneously input into the input layer 210. Assume that the learning image data set is composed of first learning image data and second learning image data, for example. In this case, the first learning image data (e.g., image data of the chest front plain X-ray image) is input into a part of the plurality of artificial neurons constituting the input layer 210, and the second learning image data (e.g., image data of the waist side plain X-ray image) is input into the other part of the artificial neurons. The output data 400 output from the output layer 230 when the learning image data set is input into the input layer 210 and reference bone density associated with the learning image data set are compared with each other.

In this example, the estimation data 120 includes image data pieces of N estimation plain X-ray images in which parts of the same person appear and the parts are in different directions. The N estimation plain X-ray images are hereinafter also collectively referred to as an "estimation plain X-ray image set".

The estimation plain X-ray image set includes a frontal image and a side image of the same person, for example. The estimation plain X-ray image set includes the waist front plain X-ray image and the knee side plain X-ray image of a certain person, for example. Image sizes of the frontal image and the side image included in the estimation plain X-ray image set may be different from each other. For example, the image size of the side image may have a smaller width than the image size of the frontal image. Image data pieces of the respective estimation plain X-ray images of the estimation plain X-ray image set are hereinafter also collectively referred to as an "estimation image data set".

In this example, in a case where bone density is estimated using the estimation data 120, N estimation image data pieces constituting the estimation image data set are simultaneously input into the input layer 210. Assume that the estimation image data set is composed of first estimation image data and second estimation image data, for example. In this case, the first estimation image data is input into a part of the plurality of artificial neurons constituting the input layer 210, and the second estimation image data is input into the other part of the artificial neurons. When the estimation image data set of a certain person is input into the input layer 210, an estimated value of bone density of the person is output from the output layer 230.

As described above, the accuracy of estimation of bone density can be improved by using the image data pieces of the plurality of plain X-ray images in which parts of the same subject appear and the parts are in different directions.

The learning data 130 may include the learning image data set and the learning health-related information. In this case, in learning of the neural network 200, the learning image data set and the learning health-related information of the same person are simultaneously input into the input layer 210. Similarly, the estimation data 120 may include the estimation image data set and the estimation health-related information. In this case, the estimation image data set and the estimation health-related information are simultaneously input into the input layer 210.

In each of the above-mentioned examples, the same learned parameter 110 is used regardless of the type of a bone appearing in an X-ray image indicated by the estimation image data, but the learned parameter 110 may be used in accordance with the type of the bone appearing in the X-ray image indicated by the estimation image data. In this case, the neural network 200 includes a plurality of learned parameters 110 in accordance with respective types of bones. The neural network 200 estimates bone density using one of the learned parameters 110 in accordance with the type of the bone appearing in the X-ray image indicated by the estimation image data as input. For example, in a case where the lumbar vertebra appears in the X-ray image indicated by the estimation image data as input, the neural network 200 estimates bone density using a learned parameter 110 for estimation of bone density of the lumbar vertebra. In a case where the proximal femur appears in the X-ray image indicated by the estimation image data as input, the neural network 200 estimates bone density using a learned parameter 110 for estimation of bone density of the proximal femur. The neural network 200 uses one of the plurality of learned parameters 110 designated by the user through the input unit 50, for example. In this case, the user designates one of the learned parameters 110 to be used by the neural network 200 in accordance with the type of the bone appearing in the X-ray image indicated by the estimation image data input into the neural network 200.

In learning of the neural network 200, a plurality of learning image data pieces indicating respective X-ray images in which bones of the same type appear are used to generate the learned parameter 110 in accordance with the type of the bones.

As described above, the estimation apparatus 1 and the bone density estimation system 600 have been described in detail, but the foregoing description is in all aspects illustrative and not restrictive. Various examples described above can be combined with each other for application unless any contradiction occurs. It is understood that numerous examples not having been described can be devised without departing from the scope of the present disclosure.

Embodiment 2

Figure 7:
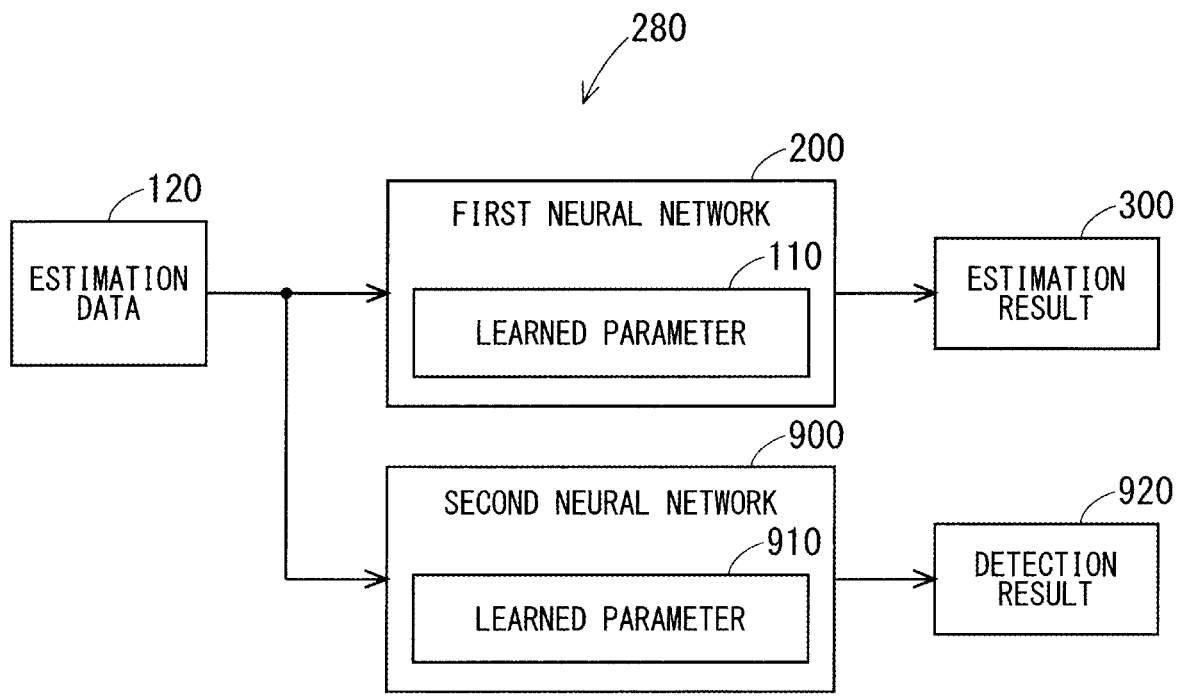
FIG. 7 illustrates a diagram showing one example of the configuration of the estimation apparatus.

FIG. 7 illustrates a diagram showing one example of a configuration of an estimation apparatus 1A in Embodiment 2. In the estimation apparatus 1A, the approximator 280 further includes a second neural network 900. The second neural network 900 can detect a fracture based on a learned parameter 910. The estimation apparatus 1A in Embodiment 2 has an equivalent configuration to the estimation apparatus 1 in Embodiment 1, and description of the equivalent configuration will be omitted. The neural network 200 described in the above-mentioned example is referred to as a first neural network 200 for convenience of description. The second neural network 900 has an equivalent configuration to the first neural network 200, for example.

The second neural network 900 can detect a fracture based on the same estimation image data as the estimation image data included in the estimation data 120 input into the first neural network 200. That is to say, from a single estimation image data piece, the first neural network 200 can estimate bone density, and the second neural network 900 can detect a fracture. A detection result 920 of the second neural network 900 is only required to be output from the output layer 230 of the second neural network 900 as in the above-mentioned example.

In learning of the second neural network 900, a parameter is learned using learning image data in which an unfractured bone appears and learning image data in which a fractured bone appears. In the supervised data, with each of the learning image data pieces, information indicating the current presence or absence of any fracture and information indicating the location of the fracture of a bone appearing in the learning image data are associated. The supervised data may include information indicating past fracture history and information indicating the location of a past fracture. As a result, the second neural network 900 can detect, based on the estimation image data, the presence or absence and the location of a fracture of a bone appearing in the estimation image data, and output the detection result 920.

Figure 8:
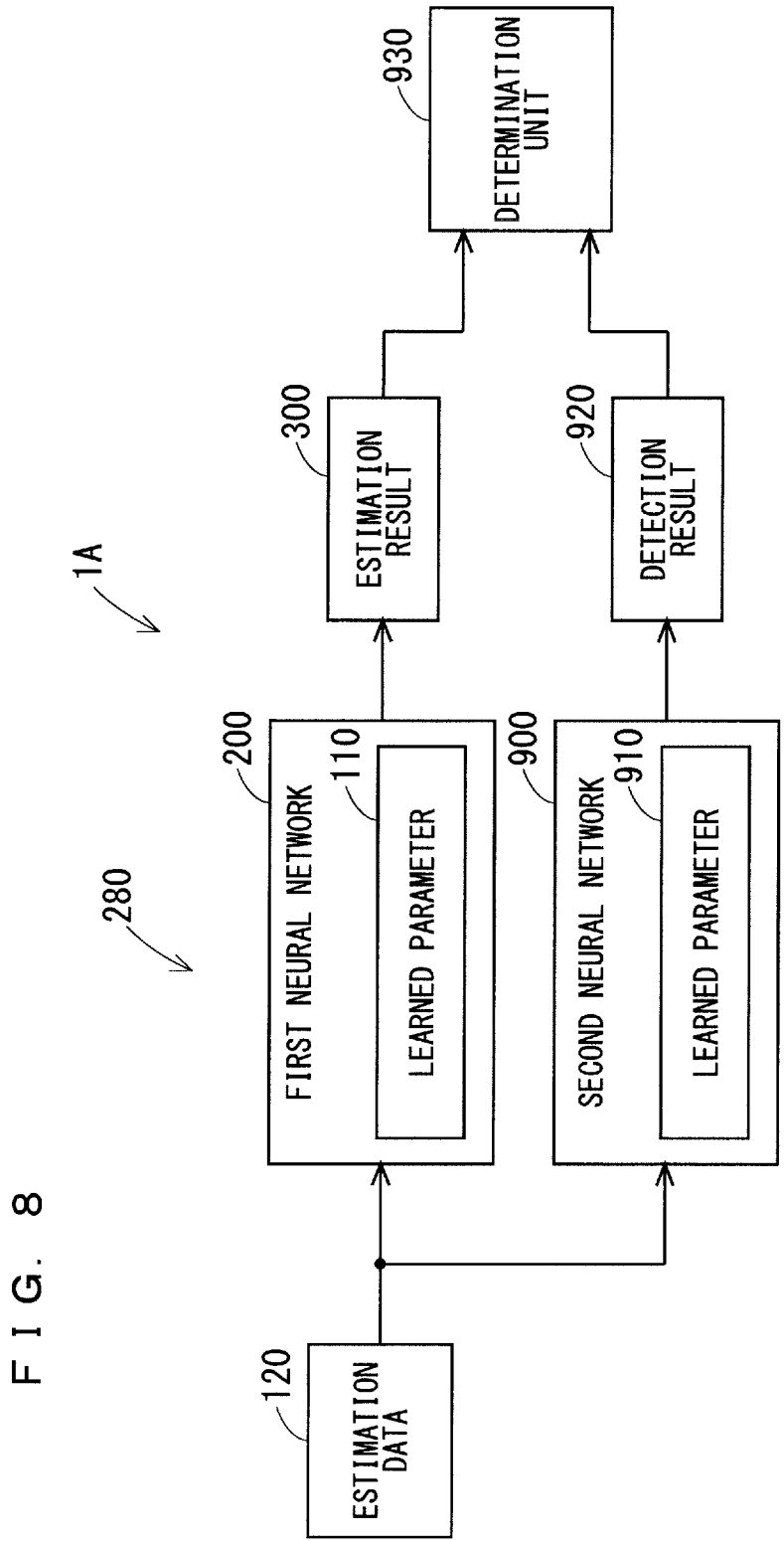
FIG. 8 illustrates a diagram showing one example of the configuration of the estimation apparatus.

The estimation apparatus 1A in Embodiment 2 may include a determination unit 930 to determine whether the subject has osteoporosis as shown in FIG. 8. The determination unit 930 can compare the estimation result 300 of the first neural network 200 and the detection result 920 of the second neural network 900 to determine whether the subject has osteoporosis.

The determination unit 900 may determine osteoporosis based on unique criteria or already known guidelines, for example. Specifically, the determination unit 900 may determine osteoporosis when the detection result 920 indicates a fracture in a vertebral body or the proximal femur. In a case where the estimated bone density value 300 output from the first neural network 200 is represented by the YAM, the determination unit 900 may determine osteoporosis when the YAM has a value of less than 80% and the detection result 920 indicates a fracture in a part other than the vertebral body and the proximal femur. The determination unit 900 may determine osteoporosis when the YAM representing the estimated bone density value 300 has a value of 70% or less.

Figure 9:
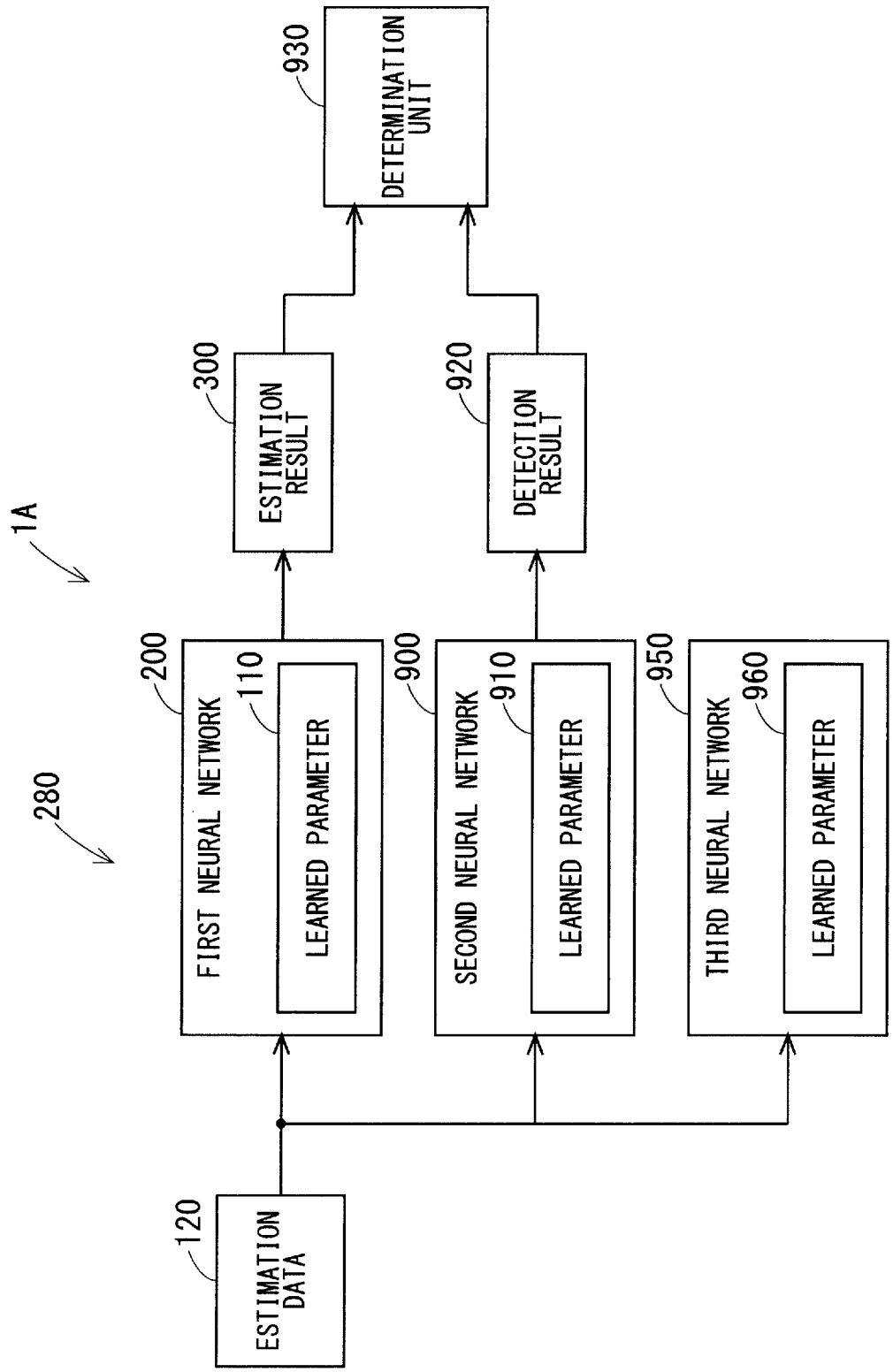
FIG. 9 illustrates a diagram showing one example of the configuration of the estimation apparatus.

In the estimation apparatus 1A in Embodiment 2, the approximator 280 may further include a third neural network 950 as shown in FIG. 9. The third neural network 950 can segment, based on a learned parameter 960, a bone of the subject from the estimation image data included in the estimation data 120.

The third neural network 950 outputs, for each of the pixels data pieces of the estimation image data as input, part information indicating a part of the bone indicated by the pixel data. The bone appearing in the X-ray image indicated by the estimation image data can thereby be segmented. The part information is also referred to as segmentation data.

In a case where the lumbar vertebra appears in the X-ray image indicated by the estimation image data as input, for example, the third neural network 950 outputs, for each of the pixels data pieces of the estimation image data, part information indicating any of parts L1 to L5 of the lumbar vertebra indicated by the pixel data. In a case where a certain pixel data of the estimation image data indicates L1 of the lumbar vertebra, for example, the third neural network 950 outputs part information indicating L1 as the part information corresponding to the pixel data.

The third neural network 950 uses the learned parameter 960 in accordance with the type of the bone appearing in the X-ray image indicated by the estimation image data. The third neural network 950 includes a plurality of learned parameters 960 in accordance with respective types of bones. The third neural network 950 segments the bone appearing in the X-ray image indicated by the estimation image data as input using the learned parameter 960 in accordance with the type of the bone appearing in the X-ray image indicated by the estimation image data. In a case where the lumbar vertebra appears in the X-ray image indicated by the estimation image data as input, for example, the third neural network 950 segments the lumbar vertebra into L1 to L5 using the learned parameter 960 in accordance with the lumbar vertebra. The third neural network 950 uses one of the plurality of learned parameters 960 designated by the user through the input unit 50, for example. In this case, the user designates one of the learned parameters 960 to be used by the third neural network 950 in accordance with the type of the bone appearing in the X-ray image indicated by the estimation image data input into the third neural network 950.

The third neural network 950 may segment the bone appearing in the X-ray image indicated by the estimation image data as input into a first part in which an implant is implanted, a second part including a tumor, and a third part including a fracture. In this case, the third neural network 950 outputs, for each of the pixels data pieces of the estimation image data, part information indicating any of the first part, the second part, and the third part indicated by the pixel data. In a case where the pixel data indicates a part other than the first part, the second part, and the third part, the third neural network 950 outputs part information indicating that the pixel data indicates the part other than the first part, the second part, and the third part. It can be said that the third neural network 950 detects the implant implanted in the bone appearing in the X-ray image indicated by the estimation image data, the fracture of the bone, and the tumor of the bone in a case where the third neural network 950 segments the bone appearing in the X-ray image indicated by the estimation image data into the first part, the second part, and the third part.

In learning of the third neural network 950, a plurality of learning image data pieces indicating respective X-ray images in which bones of the same type appear are used to generate the learned parameter 960 in accordance with the type of the bones. In a case where the third neural network 950 segments the bone appearing in the X-ray image indicated by the estimation image data as input into the first part, the second part, and the third part, the plurality of learning image data pieces include learning image data indicating an X-ray image in which a case of an implanted implant appears, learning image data indicating an X-ray image in which a case of a tumor of a bone appears, and learning image data indicating an X-ray image in which a case of a fracture appears. The supervised data includes, for each of the learning image data pieces, annotation information for segmentation of the bone indicated by the learning image data. The annotation information includes, for each of pixels data pieces of the learning image data corresponding to the annotation information, part information indicating a part of the bone indicated by the pixel data.

Figure 10:
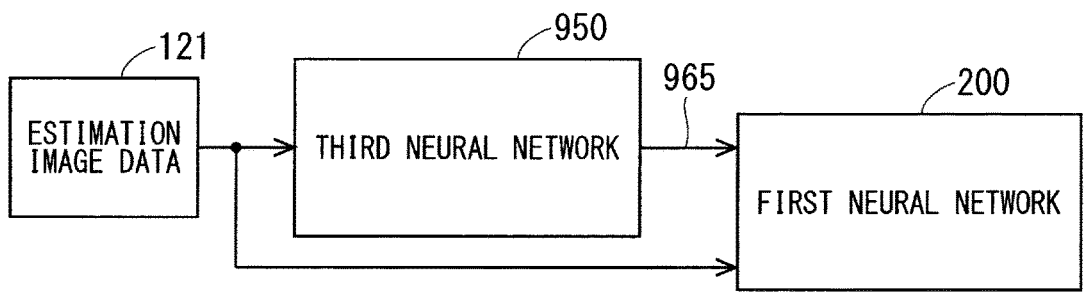
FIG. 10 illustrates a diagram showing one example of the configuration of the estimation apparatus.

The first neural network 200 may estimate bone density for each of the parts obtained by segmentation of the third neural network 950. In this case, estimation image data 121 and part information 965, for each of the pixels data pieces of the estimation image data 121, output from the third neural network 950 based on the estimation image data 121 are input into the first neural network 200 as shown in FIG. 10. The first neural network 200 outputs, for each of the parts obtained by segmentation of the third neural network, the estimated bone density value 300 of the part based on the learned parameter 110 in accordance with the type of a bone appearing in an X-ray image indicated by the estimation image data 121. In a case where the third neural network 950 segments a cervical vertebra appearing in the X-ray image indicated by the estimation image data 121 into L1 to L5, for example, the first neural network 200 outputs the estimated bone density value 300 of L1, the estimated bone density value 300 of L2, the estimated bone density value 300 of L3, the estimated bone density value 300 of L4, and the estimated bone density value 300 of L5 individually.

In learning of the first neural network 200, a plurality of learning image data pieces indicating respective X-ray images in which bones of the same type appear are used to generate the learned parameter 110 in accordance with the type of the bones. The supervised data includes, for each of the learning image data pieces, reference bone density of each of parts of a bone indicated by the learning image data.

The first neural network 200 uses one of the plurality of learned parameters 110 designated by the user through the input unit 50, for example. In this case, the user designates one of the learned parameters 110 to be used by the first neural network 200 in accordance with the type of the bone appearing in the X-ray image indicated by the estimation image data input into the first neural network 200.

Figure 11:
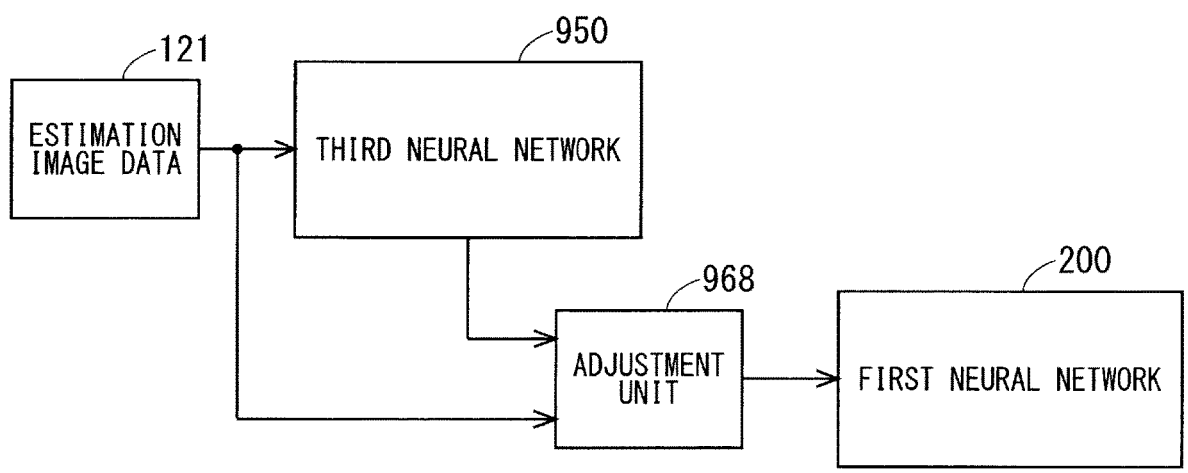
FIG. 11 illustrates a diagram showing one example of the configuration of the estimation apparatus.

In a case where the third neural network 950 segments the bone appearing in the X-ray image indicated by the estimation image data into the first part in which the implant is implanted, the second part including the tumor, and the third part including the fracture, brightness of first partial image data indicating the first part, second partial image data indicating the second part including the tumor, and third partial image data indicating the third part included in the estimation image data may be adjusted. FIG. 11 illustrates a diagram showing an example of the configuration in this case.

As shown in FIG. 11, the estimation image data 121 and the part information 965, for each of the pixels data pieces of the estimation image data 121, output from the third neural network 950 based on the estimation image data 121 are input into an adjustment unit 968. The adjustment unit 968 identifies the first partial image data, the second partial image data, and the third partial image data included in the estimation image data 121 based on the part information 965. The adjustment unit 968 adjusts brightness of the first partial image data, the second partial image data, and the third partial image data as identified.

For example, the adjustment unit 968 stores brightness of the first part appearing in a general X-ray image as first reference brightness. The adjustment unit 968 stores brightness of the second part appearing in a general X-ray image as second reference brightness. The adjustment unit 968 stores brightness of the third part appearing in a general X-ray image as third reference brightness. The adjustment unit 968 adjusts brightness of the first partial image data by subtracting the first reference brightness from brightness of the first partial image data. The adjustment unit 968 adjusts brightness of the second partial image data by subtracting the second reference brightness from brightness of the second partial image data. The adjustment unit 968 adjusts brightness of the third partial image data by subtracting the third reference brightness from brightness of the third partial image data. The adjustment unit 968 inputs the estimation image data in which brightness of the first partial image data, the second partial image data, and the third partial image data has been adjusted into the first neural network 200 as the estimation image data after brightness adjustment. The first neural network 200 estimates, based on the estimation image data after brightness adjustment, bone density of a bone appearing in an X-ray image indicated by the estimation image data.

It is herein not easy to correctly estimate bone density from the first part in which the implant is implanted, the second part including the tumor, and the third part including the fracture. As described above, bone density of the bone appearing in the X-ray image indicated by the estimation image data can more accurately be estimated by reducing brightness of the first partial image data indicating the first part, the second partial image data indicating the second part, and the third partial image data indicating the third part through adjustment.

The adjustment unit 968 may input estimation image data in which brightness of the first partial image data, the second partial image data, and the third partial image data has been forced to zero into the first neural network 200 as the estimation image data after brightness adjustment.

The third neural network 950 may detect only one of the implant, the fracture, and the tumor. The third neural network 950 may detect only two of the implant, the fracture, and the tumor. That is to say, the third neural network 950 may detect at least one of the implant, the fracture, and/or the tumor.

The estimation apparatus 1A may include the first neural network 200 and the third neural network 950 without including the second neural network 900. The estimation apparatus 1A may include at least one of the second neural network 900 and/or the third neural network 950 without including the first neural network 200.

As described above, the estimation apparatus 1A has been described in detail, but the foregoing description is in all aspects illustrative and not restrictive. Various examples described above can be combined with each other for application unless any contradiction occurs. It is understood that numerous examples not having been described can be devised without departing from the scope of the present disclosure.

Embodiment 3

Figure 12:
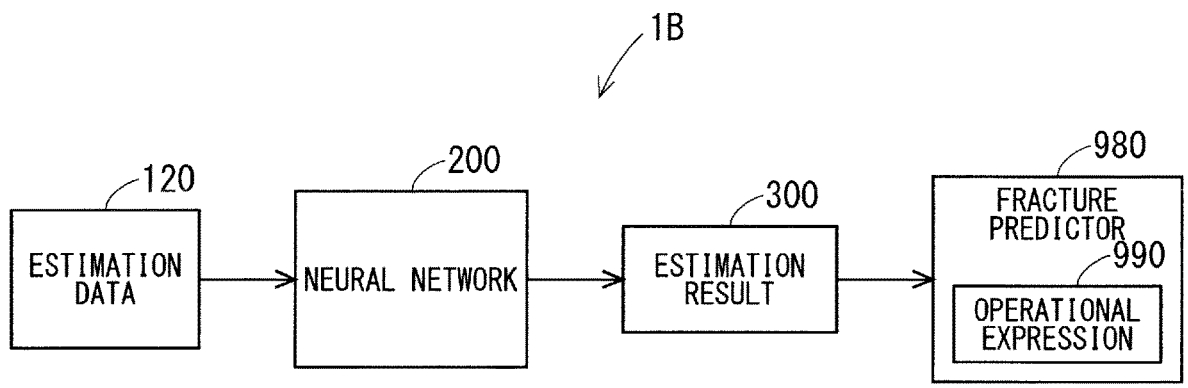
FIG. 12 illustrates a diagram showing one example of the configuration of the estimation apparatus.

FIG. 12 illustrates a diagram showing one example of a configuration of an estimation apparatus 1B in Embodiment 3. The estimation apparatus 1B includes a fracture predictor 980. The fracture predictor 980 can predict the probability of a fracture based on the estimation result 300 of the neural network 200 of the estimation apparatus 1 in Embodiment 1, for example. Specifically, an operational expression 990 indicating the relationship between an estimation result related to bone density (e.g., bone density) and the probability of the fracture is obtained from past documents and the like, for example. The fracture predictor 980 stores the operational expression 990. The fracture predictor 980 can predict the probability of the fracture based on the estimation result 300 as input and the operational expression 990 as stored.

The operational expression 990 may be an operational expression indicating the relationship between the estimation result related to bone density and the probability of a fracture after implantation of a bone screw. This allows for a study of whether to implant the bone screw and a treatment plan including drug administration.

The estimation apparatus 1B may include the second neural network 900. The estimation apparatus 1B may include the third neural network 950.

As described above, the estimation apparatus 1B has been described in detail, but the foregoing description is in all aspects illustrative and not restrictive. Various examples described above can be combined with each other for application unless any contradiction occurs. It is understood that numerous examples not having been described can be devised without departing from the scope of the present disclosure.

Embodiment 4

Figure 13:
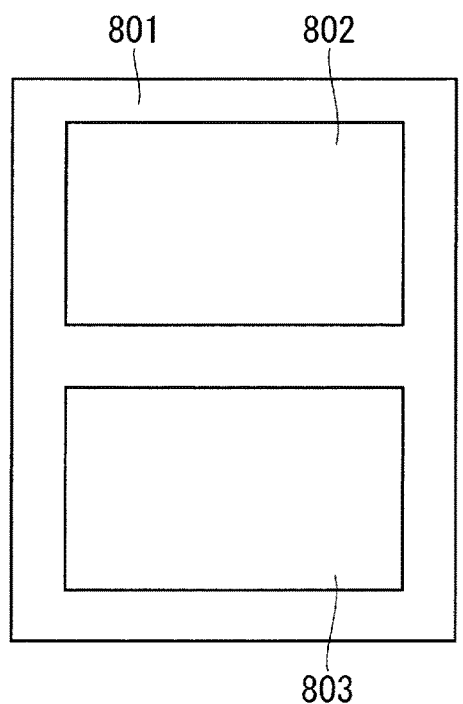
FIG. 13 illustrates a conceptual diagram schematically showing a configuration of the estimation system.

FIG. 13 illustrates the concept of a configuration of an estimation system 801 in Embodiment 4.

The estimation system 801 of the present disclosure can estimate future bone mass of the subject from an image and the like in which a bone of the subject appears, such as an X-ray image. The estimation system 801 of the present disclosure includes a terminal apparatus 802 and an estimation apparatus 803. Bone mass is an indicator related to bone density, and is the concept including bone density.

The terminal apparatus 802 can acquire input information I to be input into the estimation apparatus 803. The input information I may be an X-ray image, for example. In this case, the terminal apparatus 802 may be an apparatus for a doctor and the like to take an X-ray image of the subject. The terminal apparatus 802 may be the plain X-ray imaging apparatus (i.e., the general X-ray imaging apparatus or the radiographic imaging apparatus), for example.

The terminal apparatus 802 is not limited to the plain X-ray imaging apparatus. The terminal apparatus 802 may be an X-ray fluoroscopic imaging apparatus, computed tomography (CT), magnetic resonance imaging (MRI), single photon emission computed tomography(SPECT)-CT, or tomosynthesis, for example. In this case, the input information I may be an X-ray fluoroscopic image, a computed tomography (CT) image, a magnetic resonance imaging (MRI) image, a bone scintigraphy image, or a tomosynthesis image, for example.

The estimation system 801 is used for a diagnosis of osteoporosis and the like of a patient attending a hospital, for example. The estimation system 801 of the present disclosure takes a radiograph of a patient using the terminal apparatus 802 installed in an X-ray room, for example. Image data is transferred from the terminal apparatus 802 to the estimation apparatus 803, and, through the estimation apparatus 803, not only current bone mass or bone density of the patient but also future bone mass or bone density of the patient after imaging can be estimated.

The terminal apparatus 802 may not directly transfer the input information I to the estimation apparatus 803. In this case, the input information I acquired by the terminal apparatus 802 may be stored in a storage medium, and the input information I may be input into the estimation apparatus 803 through the storage medium, for example.

FIG. 14 illustrates the concept of a configuration of the estimation apparatus 803 in Embodiment 4.

The estimation apparatus 803 can estimate future bone mass or bone density of the subject based on the input information I acquired by the terminal apparatus 802. The estimation apparatus 803 can estimate future bone mass or bone density of the subject from the image data acquired by the terminal apparatus 802, and output an estimation result O.

The estimation apparatus 803 includes an input unit 831, an approximator 832, and an output unit 833. The input unit 831 is a unit into which the input information I is input from the terminal apparatus 802. The approximator 832 can estimate future bone mass or bone density based on the input information I. The output unit 833 can output the estimation result O predicted by the approximator 832.

The estimation apparatus 803 includes various electronic parts and circuits. As a result, the estimation apparatus 803 can form components thereof. For example, the estimation apparatus 803 can form functional components of the estimation apparatus 803 by integrating a plurality of semiconductor elements to form at least one integrated circuit (e.g., an integrated circuit (IC) and large scale integration (LSI)), or further integrating a plurality of integrated circuits to form at least one unit, for example.

The electronic parts may be active elements, such as transistors and diodes, or passive elements, such as capacitors. The electronic parts, the IC formed by integrating the electronic parts, and the like can be formed by a conventionally known method.

The input unit 831 is a unit into which information to be used by the estimation apparatus 803 is input. The input information I including the X-ray image acquired by the terminal apparatus 802 is input into the input unit 831, for example. The input unit 831 includes a communication unit, and the input information I acquired by the terminal apparatus 802 is directly input from the terminal apparatus 802. The input unit 831 may include an input device into which the input information I or other information pieces can be input. The input device may be a keyboard, a touch panel, a mouse, and the like, for example.

The approximator 832 estimates future bone mass or bone density of the subject based on the information input into the input unit 831. The approximator 832 includes artificial intelligence (AI). The approximator 832 includes a program functioning as the AI and various electronic parts and circuits to execute the program. The approximator 832 includes the neural network.

The approximator 832 is subjected to a learning process on the relationship between input and output in advance. That is to say, machine learning is applied to the approximator 832 using the learn data and the supervised data, so that the approximator 832 can calculate the estimation result O from the input information I. The learn data or the supervised data is only required to be data corresponding to the input information I input into the estimation apparatus 803 and the estimation result O output from the estimation apparatus 803.

FIG. 15 illustrates the concept of a configuration of the approximator 832 of the present disclosure.

The approximator 832 includes a first neural network 8321 and a second neural network 8322. The first neural network 8321 is only required to be a neural network suitable for handling of chronological information. The first neural network 8321 may be a ConvLSTM network as a combination of long short-term memory (LSTM) and a convolutional neural network (CNN), for example. The second neural network 8322 may be a convolutional neural network including a CNN, for example.

The first neural network 8321 includes an encoder E and a decoder D. The encoder E can extract a feature of a temporal change of the input information I and location information. The decoder D can calculate, based on the feature extracted by the encoder E, and the temporal change and an initial value of the input information I, a new feature.

Figure 16:
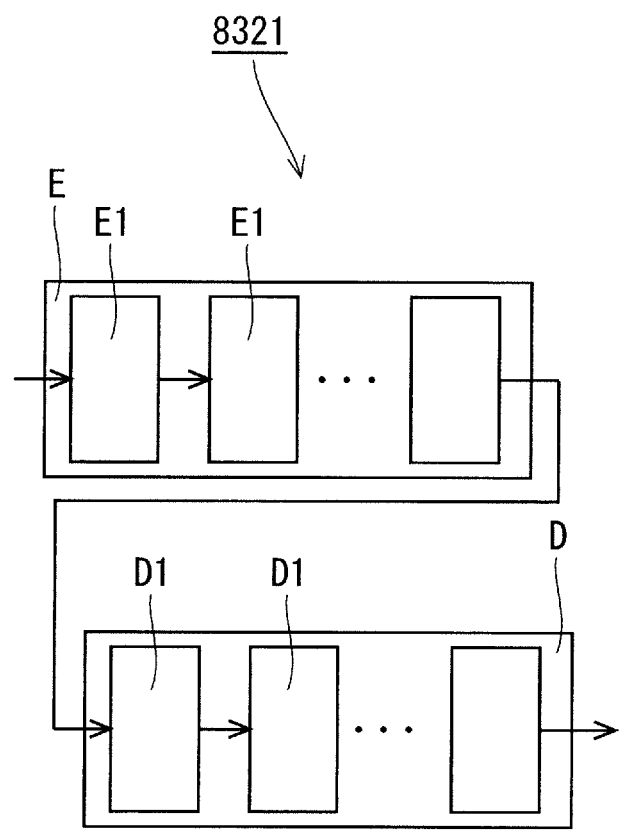
FIG. 16 illustrates a conceptual diagram schematically showing a configuration of a portion of the estimation system.

FIG. 16 illustrates the concept of a configuration of the first neural network 8321 of the present disclosure.

The encoder E includes a plurality of convolutional long short-term memory (ConvLSTM) layers E1. The decoder D includes a plurality of convolutional long short-term memory (ConvLSTM) layers D1. Each of the encoder E and the decoder D may include three or more ConvLSTM layers E1 or D1. The number of ConvLSTM layers E1 and the number of ConvLSTM layers D1 may be the same.

The plurality of ConvLSTM layers E1 may learn different contents. The plurality of ConvLSTM layers D1 may learn different contents. For example, a certain ConvLTSM layer learns a detailed content, such as a change of each pixel, and another ConvLTSM layer learns a general content, such as a change of a whole picture.

FIG. 17 illustrates the concept of a configuration of the second neural network 8322.

The second neural network 8322 includes a converter C. The converter C can convert the feature calculated by the decoder D of the first neural network 8321 into bone mass or bone density. The converter C includes a plurality of convolutional layers C1, a plurality of pooling layers C2, and a fully connected layer C3. The fully connected layer C3 precedes an output unit 33. In the converter C, the convolutional layers C1 and the pooling layers C2 are alternately arranged between the first neural network 8321 and the fully connected layer C3.

The learn data is input into the encoder E of the approximator 832 when the approximator 832 is learned. The supervised data is compared with output data output from the converter C of the approximator 832 when the approximator 832 is learned. The supervised data is data indicating a value measured using a conventional bone density measurement apparatus.

The output unit 833 can display the estimation result O. The output unit 833 is a liquid crystal display or an organic EL display, for example. The output unit 833 can display various pieces of information, such as characters, symbols, and graphics. The output unit 833 can display figures or images, for example.

The estimation apparatus 803 of the present disclosure further includes a controller 834 and a storage 835. The controller 834 can provide overall management of operation of the estimation apparatus 803 through control of the other components of the estimation apparatus 803.

The controller 834 includes a processor, for example. The processor may include one or more processors, controllers, microprocessors, microcontrollers, application specific integrated circuits (ASICs), digital signal processors, programmable logic devices, or a combination of these devices or any structures, or other known devices and structures, for example. The controller 834 includes a CPU, for example.

The storage 835 includes a non-transitory recording medium readable by the CPU of the controller 834, such as random access memory (RAM) and read only memory (ROM), for example. A control program to control the estimation apparatus 803, such as firmware, is stored in the storage 835. The input information I to be input, the learn data to be learned, and the supervised data may be stored in the storage 835.

The processor of the controller 834 can perform one or more data computing procedures or processes in accordance with the control program in the storage 835. Various functions of the controller 834 are performed by the CPU of the controller 834 executing the control program in the storage 835.

The controller 834 may perform other processes as necessary as preprocesses of a computing process.

Examples of Input Information, Learn Data, and Supervised Data

The input information (hereinafter, also referred to as first input information I1) includes image data in which a bone of a target of estimation of bone mass or bone density appears. The image data may be a plain X-ray image, for example. The target of estimation of bone mass or bone density is a person, for example. In this case, it can be said that the first input information I1 is image data of a plain X-ray image in which a bone of a person appears. The plain X-ray image is a two-dimensional image, and is also referred to as the general X-ray image or the radiographic image.

The first input information I1 is preferably the plain X-ray image, which is relatively easily available, but is not limited to the plain X-ray image. Bone mass or bone density can be estimated more accurately in some cases by using the X-ray fluoroscopic image, the computed tomography (CT) image, the magnetic resonance imaging (MRI) image, the bone scintigraphy image, or the tomosynthesis image as the input information, for example.

The target of estimation of bone mass or bone density may not be a person. The target of estimation of bone mass or bone density may be an animal, such as a dog, a cat, and a horse. A bone of interest mainly includes a cortical bone and a cancellous bone derived from organisms, but may include an artificial bone containing calcium phosphate as a main component and a regenerated bone artificially manufactured by regenerative medicine and the like.

The imaging part of the X-ray image may be the neck, the chest, the waist, the proximal femur, the knee joint, the ankle joint, the shoulder joint, the elbow joint, the wrist joint, an interphalangeal joint, or the temporomandibular joint, for example. A part other than a bone may appear in the X-ray image. In a case of the chest plain X-ray image, for example, an image of the lung and an image of the thoracic vertebra may be included. The X-ray image may be the frontal image in which the front of the part of interest appears or the side image in which the side of the part of interest appears.

The learn data or the supervised data is only required to be data corresponding to the input information I input into the estimation apparatus 803 and the estimation result O output from the estimation apparatus 803.

The learn data includes information of the same type as the first input information I1. If the first input information I1 is the plain X-ray image, for example, the learn data is only required to include the plain X-ray image. Furthermore, if the first input information I1 is the chest plain X-ray image, for example, the learn data is only required to include the chest plain X-ray image.

The learn data includes learning image data pieces of a plurality of plain X-ray images in each of which a bone appears. An imaging part of each of the learning image data pieces includes at least one of the neck, the chest, the waist, the proximal femur, the knee joint, the ankle joint, the shoulder joint, the elbow joint, the wrist joint, the interphalangeal joint, and/or the temporomandibular joint, for example. The learn data may include some or all of the 11 types of image data. The learning image data pieces may include the frontal image or the side image.

Bones of a plurality of different people appear in the learn data. With each of the learning image data pieces, an actual value of bone mass or bone density of the subject of the learning image data is associated as the supervised data. The actual value of bone mass or bone density is measured in approximately the same time period as a time period in which the learning image data is taken.

The learning image data pieces of the learn data may be a series of data pieces of the same person taken at different points in time. That is to say, the learning image data pieces may include first learn data including an X-ray image of a bone and second learn data including the X-ray image which is taken after the X-ray image of the first learn data and is an X-ray image of the same person as the X-ray image of the first learn data.

The learning image data pieces of the learn data may be a group of data pieces of the same part of other people differing in age and the like. The learning image data pieces of the learn data may be a series of data pieces of the same part of the same person taken at different points in time.

Data obtained by reducing grayscale image data indicating a plain X-ray image taken by the plain X-ray imaging apparatus (i.e., the general X-ray imaging apparatus or the radiographic imaging apparatus) and reducing the number of gray levels thereof may be used as the learn data and the first input information I1. Consider a case where the number of pixels data pieces of the image data is greater than 1024× 640, and the number of bits of the pixel data pieces is 16, for example. In this case, data obtained by reducing the number of pixels data pieces to 256×256, 1024×512, or 1024×640, and reducing the number of bits of the pixel data pieces to 8, for example, is used as the first input information I1 and the learn data.

The supervised data includes, for each of the learning image data pieces included in the learn data, a measured value of bone mass or bone density of a person having a bone appearing in a learning plain X-ray image indicated by the learning image data. Bone mass or bone density is only required to be measured by the dual-energy X-ray absorptiometry (DEXA) or the ultrasonic method, for example.

Example of Learning of Neural Network

The controller 834 performs machine learning on the approximator 832 using the learn data and the supervised data so that the approximator 832 can calculate the estimation result O related to bone mass or bone density from the input information I. The approximator 832 is optimized by known machine learning using the supervised data. The approximator 832 adjusts a variable parameter in the approximator 832 to reduce an error, from the supervised data, of a spurious estimation result operated from the learn data input into the encoder E and output from the converter C.

Specifically, the controller 834 inputs the learn data in the storage 835 into the encoder E. When inputting the learn data into the encoder E, the controller 834 inputs a plurality of pixel data pieces constituting each of the learning image data pieces into respective artificial neurons constituting the encoder E. The controller 834 adjusts the parameter to reduce an error, from the actual value of bone mass or bone density associated with the learning image data, of the estimation result O output from the converter C when the learning image data is input into the encoder E. The parameter as adjusted is stored in the storage 835 as the learned parameter.

Backpropagation is used as a method for adjusting the parameter, for example. The parameter includes a parameter used in the encoder E, the decoder D, and the converter C, for example. Specifically, the parameter includes a weighting factor used in the ConvLSTM layers of the encoder E and the decoder D and the convolutional layers and the fully connected layer of the converter C.

As a result, the approximator 832 performs operations based on the learned parameter on the input information I input into the encoder E, and outputs the estimation result O from the converter C. When X-ray image data as the input information I is input into the encoder E, a plurality of pixel data pieces constituting the image data are input into respective artificial neurons constituting the input unit 831. The ConvLSTM layers, the convolutional layers, and the fully connected layer can perform operations using the weighting factor included in the learned parameter to output the estimation result O.

As described above, in the estimation system 801, learning of the approximator 832 and estimation of bone mass or bone density by the approximator 832 are performed using the image data of the plain X-ray image. Future bone mass or bone density can thus be output as the estimation result O through input of the input information I into the estimation system 801.

The estimation result O of the estimation system 801 is only required to be an estimation result on a certain day after a day of acquisition of the input information I. For example, the estimation system 1 can estimate bone mass or bone density three months to 50 years, preferably six months to 10 years, after imaging.

The estimation result O may be output as a value. The estimation result O may be represented by at least one of the young adult mean (YAM), the T-score, and/or the Z-score, for example. For example, an estimated value represented by the YAM may be output from the output unit 833, or an estimated value represented by the YAM, an estimated value represented by the T-score, and an estimated value represented by the Z-score may be output from the output unit 833.

The estimation result O may be output as an image. In a case where the estimation result O is the image, an X-ray image-like image may be displayed, for example. The X-ray image-like image is an image mimicking an X-ray image. In a case where a series of data pieces of the same part of the same person taken at different points in time are learned using ConvLSTM, a temporal change of the image can be predicted. A future image can thereby be generated from an X-ray image of a different patient at a single point in time.

In addition to a bone, viscera, muscles, fats, or blood vessels may appear in the learn data and the input information I. More accurate estimation can be performed also in this case.

The first input information I1 may include the individual data (first individual data) of the test subject. The first individual data may be the age information, the gender information, the height information, the weight information, and the fracture history, for example. As a result, more accurate estimation can be performed.

The first input information I1 may include second individual data of the test subject. The second individual data may include information on blood pressure, a lipid, cholesterol, neutral fats, and a blood sugar level, for example. As a result, more accurate estimation can be performed.

The first input information I1 may include living habit information of the test subject. The living habit information may be information on a drinking habit, a smoking habit, an exercise habit, a dietary habit, and the like. As a result, more accurate estimation can be performed.

The first input information I1 may include bone turnover information of the test subject. The bone turnover information may be a bone resorption capability or a bone formation capability, for example. They can be measured by at least one of type I collagen cross-linked N-telopeptide (NYX), type I collagen cross-linked C-telopeptide (CTX), tartrate-resistant acid phosphatase 5b (TRACP-5b), and deoxypyridinoline (DPD) as a bone resorption maker, bone specific alkaline phosphatase (BAP) and type I collagen cross-linked N-propeptide (P1NP) as a bone formation maker, and/or undercaroxylated osteocalcin (ucOC) as a bone-related matrix maker, for example. The bone resorption maker may be measured using serum or urine as an analyte.

In the estimation system 801, second input information I2 related to future scheduled action of the subject may further be input as the input information I. The second input information I2 may be individual data to be improved or after improvement or information related to the living habit, the exercise habit, and the dietary habit to be improved or after improvement, for example. Specifically, the second input information I2 may be information on weight data, the drinking habit, the smoking habit, a time of exposure to the sun, the number of steps or a walking distance per day, intake of daily products, and intake of food having a high content of vitamin D, such as fish and mushrooms, after improvement. As a result, the estimation system 801 can indicate the estimation result O of future bone mass or bone density as improved.

The second input information I2 may be information related to a living habit to be worsened, for example. As a result, the estimation system can indicate the estimation result O of future bone mass or bone density as worsened.

In the estimation system 801, third input information I3 related to therapy for the subject may further be input as the input information I. The third input information I3 is information related to physical therapy or drug therapy, for example. Specifically, the third input information I3 may be at least one of a calcium drug, a female hormone drug, a vitamin drug, a bisphosphonate drug, a selective estrogen receptor modulator (SERM) drug, a calcitonin drug, a thyroid hormone drug, and/or a denosumab drug.

In the estimation system 801, a first result O1 based only on the first input information I1 and a second result O2 based on the first input information I1 and at least one of the second input information I2 and/or the third input information I3 may be output as the estimation result O. As a result, effects on the future scheduled action can be compared.

In the estimation system 801, not only future bone mass or bone density but also a result under the present circumstances may be output as the estimation result O. As a result, changes over time of bone mass or bone density can be compared.

FIG. 18 illustrates the concept of a configuration of the approximator 832 in another embodiment of the disclosure of the estimation system 1.

The estimation apparatus 803 of the estimation system 801 may include a first approximator 832a and a second approximator 832b. That is to say, the estimation apparatus 803 may include the second approximator 832b in addition to the above-mentioned approximator 832 (first approximator 832a). The second approximator 832b may be a CNN, for example.

In this case, the first approximator 832a outputs a first image and a first value to a first output unit 833a as a first estimation result O1 in the estimation system 801. Furthermore, the second approximator 832b outputs, from the first image from the first output unit 833a, a second value to a second output unit 833b as a second estimation result O2. As a result, the first value and the second value can be compared with each other as the estimation result O of future bone mass or bone density.

The estimation system 801 may output, as the estimation result O, a third value based on the first value and the second value. As a result, a result (the third value) of correction of the first value based on the second value can be set to the estimation result O, for example.

As described above, the estimation system 801 has been described in detail, but the foregoing description is in all aspects illustrative and not restrictive. Various examples described above can be combined with each other for application unless any contradiction occurs. It is understood that numerous examples not having been described can be devised without departing from the scope of the present disclosure.

The invention claimed is:

1. An estimation apparatus comprising at least one processor communicatively coupled with at least one non-transitory computer readable medium, wherein the at least one processor is programmed to:
receive input information including a first image of a first portion of a skeleton of a first person, where the first image is a plain X-ray image obtained from X-rays transmitted through the first portion of the skeleton of the first person from only a single direction, and where the first image does not include a multiple-material phantom; and
estimate a bone density of the first person based on the first image of the first portion of the skeleton of the first person and a trained parameter,
wherein the trained parameter is generated by a neural network based on one or more second X-ray images of a skeleton of one or more second persons and supervised data comprising a known bone density corresponding to each second image.

2. The estimation apparatus according to claim 1, wherein the bone density of the one or more second persons is measured by anteroposterior X-ray irradiation.

3. The estimation apparatus according to claim 1, wherein the supervised data includes one or more third X-ray images of the skeleton of the one or more second persons and a known bone density corresponding to each third X-ray image, wherein a portion of the skeleton of the one or more second persons in the one or more third X-ray images is different from the portion of the skeleton of the one or more second persons in the one or more second X-ray images.

4. The estimation apparatus according to claim 1, wherein
the input information further includes a first image set of a plurality first images of the first portion of the skeleton of the first person taken from different directions,
the plurality of first images in the first image set are input into the estimation apparatus in parallel,
the supervised data further includes a second image set of a plurality of second images of the skeleton of the one or more second persons taken from different directions.

5. The estimation apparatus according to claim 4, wherein the first image set includes at least one anteroposterior image and at least one lateral image.

6. The estimation apparatus according to claim 1, wherein at least a portion of the one or more second X-ray images of the skeleton of the one or more second persons are of a different portion of a skeleton than the first image of the first portion of the skeleton of the first person.

7. The estimation apparatus according to claim 1, wherein at least a portion of the one or more second X-ray images of the skeleton of the one or more second persons are of a same portion of a skeleton as the first image of the first portion of the skeleton of the first person.

8. The estimation apparatus according to claim 1, wherein the one or more second X-ray images is a plain X-ray image.

9. The estimation apparatus according to claim 1, wherein the supervised data includes a bone density corresponding to a bone appearing in the one or more second X-ray images of the skeleton of the one or more second persons.

10. The estimation apparatus according to claim 1, wherein the supervised data includes a plurality of second images of a plurality of portions of the skeleton of the one or more second persons, the plurality of portions of the skeleton of the one or more second persons including the first portion of the skeleton of the one or more second persons.

11. The estimation apparatus according to claim 1, wherein the supervised data includes a bone density for each of a plurality of training images of the one or more second persons.

12. The estimation apparatus according to claim 1, wherein the one or second X-ray images of the skeleton of one or more second persons and the known bone density corresponding to each second image are obtained in a same time period.

13. The estimation apparatus according to claim 1, wherein
the one or more second X-ray images of the skeleton of the one or more second persons is of a same portion of a skeleton as the first portion of the skeleton of the first person, and
the first image of the first portion of the skeleton of the first person is taken from a first direction,
the one or more second X-ray images of the skeleton of the one or more second persons is taken from a second direction, where the first direction and the second direction are different.

14. The estimation apparatus according to claim 1, wherein
the one or more second X-ray images of the skeleton of the one or more second persons is of a same portion of a skeleton as the first portion of the skeleton of the first person, and
the first image of the first portion of the skeleton of the first person is taken from a first direction,
the one or more second X-ray images of the skeleton of the one or more second persons is taken from a second direction, where the first direction and the second direction are the same.

15. The estimation apparatus according to claim 1, wherein the supervised data includes information related to a health condition of the one or more second persons.

16. The estimation apparatus according to claim 15, wherein the information related to the health condition includes at least one of drinking habit information, smoking habit information, and fracture history information.

17. The estimation apparatus according to claim 1, wherein the supervised data further includes a plurality of additional X-ray images of the skeleton of the one or more second persons taken from different directions.

18. The estimation apparatus according to claim 1, wherein the supervised data further includes a plurality of additional X-ray images of the skeleton of the one or more second persons taken at different times.

19. The estimation apparatus according to claim 1, wherein the supervised data includes a plurality of additional X-ray images of the skeleton of a plurality of second persons, the plurality of second persons including the one or more second persons.

20. The estimation apparatus according to claim 1, wherein the supervised data includes a bone density of at least one of a lumbar vertebra, a proximal femur, a radius, a hand bone, a tibia, and a calcaneus.

21. The estimation apparatus according to claim 1, wherein the supervised data includes a bone density measured based on at least one of dual-energy X-ray absorptiometry and an ultrasonic method.

22. The estimation apparatus according to claim 1, wherein
the one or more second X-ray images is a plain X-ray image of the skeleton of the one or more second persons,
the supervised data includes a bone density of the skeleton of the one or more second persons measured by dual-energy X-ray absorptiometry, and
a direction of X-ray irradiation in taking the one or more second X-ray images is the same as a direction of X-ray irradiation in measurement of the known bone density of the skeleton of the one or more second persons.

23. The estimation apparatus according to claim 1, wherein the supervised data includes a bone density of a lumbar vertebra.

24. The estimation apparatus according to claim 1, wherein the supervised data includes a bone density of a proximal femur.

25. The estimation apparatus according to claim 1, wherein the first image is an anteroposterior image of a lumbar vertebra or a chest.

26. The estimation apparatus according to claim 1, wherein the first image is a knee joint image.

27. The estimation apparatus according to claim 1, wherein the first image is obtained by reducing a number of pixels of an image taken by a plain X-ray imaging apparatus.

28. The estimation apparatus according to claim 1, wherein the first image is obtained by reducing gray levels of an image taken by a plain X-ray imaging apparatus.

29. The estimation apparatus according to claim 1, wherein the bone density of the first person includes at least one of bone mineral density per unit area (g/cm$^2$), bone mineral density per unit volume (g/cm$^3$), young adult mean (YAM), a T-score, and/or a Z-score.

30. An estimation apparatus comprising at least one processor communicatively coupled with at least one non-transitory computer readable medium, wherein the at least one processor is programmed to:
receive input information including a first image of a first portion of a skeleton of a first person, where the first image is a plain X-ray image obtained from X-rays transmitted through the first portion of the skeleton of the first person from only a single direction; and
estimate a bone density of the first person based on the first image of the skeleton of the first person and a trained parameter,
wherein the trained parameter is generated by a neural network based on one or more second X-ray images of a skeleton of one or more second persons and supervised data comprising a known bone density corresponding to each second image, and
wherein a direction of X-ray irradiation in taking at least a portion of the one or more second X-ray images is different from a direction of X-ray irradiation in measurement of the known bone density of the corresponding at least a portion of the one or more second X-ray images.

31. A system comprising:
the estimation apparatus according to claim 1; and
a display configured to display a result of an estimation of bone density obtained by the estimation apparatus.

32. An estimation system comprising at least one processor communicatively coupled with at least one non-transitory computer readable medium, wherein the at least one processor is programmed to:
receive one or more training X-ray images of a first portion of a skeleton of one or more persons;
receive supervised data including a bone density corresponding to each of the one or more training X-ray images;
generate a trained parameter based on an analysis of the one or more training X-ray images and the corresponding bone densities;
receive a first image of a first portion of a skeleton of a first person, wherein the first image is a plain X-ray image obtained from X-rays transmitted through the first portion of the skeleton of the first person from only an anteroposterior direction, and wherein the first image does not include a multiple-material phantom; and
estimate a bone density of the first person based on the first image of the skeleton of the first person and the trained parameter.

33. A system for estimating bone density comprising:
a training apparatus comprising at least one processor communicatively coupled with at least one non-transitory computer readable medium, wherein the at least one processor is programmed to:
receive one or more training X-ray images of a skeleton of one or more persons and a known bone density corresponding to each training X-ray image, and
generate a trained parameter based on an analysis of the one or more training X-ray images and the corresponding bone densities;
an estimation apparatus comprising at least one processor communicatively coupled with at least one non-transitory computer readable medium, wherein the at least one processor is programmed to:
receive input information including a first image of a first portion of a skeleton of a first person, where the first image is a two-dimensional X-ray image comprising image data obtained from X-rays transmitted through the first portion of the skeleton of the first person from only an anteroposterior direction, and wherein the first image does not include a multiple-material phantom, and
estimate a bone density of the first person based on the first image of the skeleton of the first person and the trained parameter.

\* \* \* \* \*